United States Patent
He et al.

(10) Patent No.: US 11,213,272 B2
(45) Date of Patent: Jan. 4, 2022

(54) SYSTEMS AND METHODS FOR MONITORING A MEDICAL DEVICE

(71) Applicant: SHANGHAI UNITED IMAGING HEALTHCARE CO., LTD., Shanghai (CN)

(72) Inventors: Tao He, Shanghai (CN); Jiawen Zhou, Shanghai (CN); Zhouyuan Fan, Shanghai (CN); Bing Li, Shanghai (CN); Pei Zhou, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 16/881,057

(22) Filed: May 22, 2020

(65) Prior Publication Data

US 2020/0281557 A1    Sep. 10, 2020

Related U.S. Application Data

(62) Division of application No. 16/138,930, filed on Sep. 21, 2018, now Pat. No. 10,660,601.

(30) Foreign Application Priority Data

Jan. 2, 2018  (CN) .......................... 201810002614.1
Jan. 2, 2018  (CN) .......................... 201810002878.7

(51) Int. Cl.
*G01D 18/00*  (2006.01)
*A61B 6/00*  (2006.01)
(Continued)

(52) U.S. Cl.
CPC ................ *A61B 6/586* (2013.01); *A61B 6/06* (2013.01); *A61B 6/4021* (2013.01);
(Continued)

(58) Field of Classification Search
CPC ......... A61B 6/586; A61B 6/4021; A61B 6/06; A61B 6/5205; A61B 6/582; A61B 6/4266; A61B 6/54; A61B 6/032
See application file for complete search history.

(56) References Cited

U.S. PATENT DOCUMENTS 4,628,522 A * 12/1986 Ebersberger ........ F16C 32/0442
                                                   310/90.5
4,853,946 A    8/1989 Elliott et al.
(Continued)

FOREIGN PATENT DOCUMENTS

CN    102770077 A    11/2012
CN    104027127 A    9/2014
(Continued)

OTHER PUBLICATIONS

The First Office Action in Chinese Application No. 201810902614,1 dated Jun. 29, 2020, 22 pages.

*Primary Examiner* — Kiho Kim
(74) *Attorney, Agent, or Firm* — Metis IP LLC

(57) ABSTRACT

The present disclosure is related to systems and methods for monitoring a medical device. The medical device may include a tube configured to generate radiation rays and a detector configured to receive radiation rays emitted from the tube. The tube may include an anode target and a filament. The detector may include a plurality of detecting units. The method may include obtaining imaging data acquired by the detector via detecting radiation rays emitted from the tube. The method may also include determining a first feature parameter associated with the radiation rays based on the imaging data. The method may further include monitoring the medical device based on the first feature parameter associated with the radiation rays.

20 Claims, 20 Drawing Sheets

(51) Int. Cl.
*A61B 6/06* (2006.01)
*A61B 6/03* (2006.01)

(52) U.S. Cl.
CPC ............ *A61B 6/5205* (2013.01); *A61B 6/582* (2013.01); *A61B 6/032* (2013.01); *A61B 6/4266* (2013.01); *A61B 6/54* (2013.01)

(56) References Cited

U.S. PATENT DOCUMENTS

| | | |
|---|---|---|
| 9,299,171 B2 | 3/2016 | Bredno et al. |
| 9,904,998 B2 | 2/2018 | Jockel et al. |
| 2006/0193428 A1 | 8/2006 | Heismann |
| 2010/0166146 A1 | 7/2010 | Tomisaki |
| 2011/0019793 A1 | 1/2011 | Honda et al. |
| 2011/0243413 A1 | 10/2011 | Tkaczyk et al. |
| 2013/0070903 A1* | 3/2013 | Behling ................ G01M 1/365 378/135 |
| 2013/0343515 A1* | 12/2013 | Besson ................ G01N 23/04 378/16 |
| 2015/0177391 A1 | 6/2015 | Cox |
| 2015/0219774 A1 | 8/2015 | Hannemann et al. |
| 2017/0258412 A1 | 9/2017 | Daerr et al. |
| 2017/0281118 A1 | 10/2017 | Hirayu |
| 2018/0082818 A1 | 3/2018 | Meiler et al. |
| 2018/0160989 A1 | 6/2018 | Herrmann |

FOREIGN PATENT DOCUMENTS

| | | |
|---|---|---|
| CN | 106526216 A | 3/2017 |
| CN | 107184227 A | 9/2017 |
| JP | 2014170643 A * | 9/2014 |

* cited by examiner

SYSTEMS AND METHODS FOR MONITORING A MEDICAL DEVICE

CROSS-REFERENCE TO RELATED APPLICATIONS

This application is a division of U.S. application Ser. No. 16/138,930, filed on Sep. 21, 2018, which claims priority of Chinese Patent Application No. 201810002614.1 filed on Jan. 2, 2018, and Chinese Patent Application No. 201810002878.7, filed on Jan. 2, 2018. Each of the above-referenced applications is expressly incorporated herein by reference in their entireties.

TECHNICAL FIELD

This disclosure generally relates to a medical imaging system, and more particularly, relates to systems and methods for monitoring a medical device in the medical imaging system.

BACKGROUND

Medical imaging system, such as an X-ray imaging device has been widely used in clinical examinations and medical diagnoses in recent years. The X-ray imaging device (e.g., a medical X-ray diagnostic device, a medical X-ray treatment device, a computed tomography (CT) device, etc.) may scan an object using radiation rays and generate one or more images relating to the object. During long-term operation of an X-ray imaging device, malfunctions such as a filament and unstable speed of an anode target, may occur due to mechanical wear, improper component replacement, or improper user operation, which may reduce the efficiency of the X-ray imaging device and threaten the safety of an operator (e.g., a doctor, a technician). At present, the malfunctions in an X-ray imaging device may be detected after the malfunctions are generated. Therefore, it is desirable to provide systems and methods for monitoring the medical device in real time and predicting the malfunctions in the medical device.

SUMMARY

According to an aspect of the present disclosure, a system for monitoring a medical device including a computer-readable storage medium storing executable instructions, and at least one processor in communication with the computer-readable storage medium. The medical device may include a tube configured to generate radiation rays and a detector configured to receive radiation rays emitted from the tube. The tube may include an anode target and a filament. The detector may include a plurality of detecting units. When executing the executable instructions, the at least one processor may be configured to cause the system to obtain imaging data acquired by the detector via detecting radiation rays emitted from the tube. The at least one processor may also cause the system to determine a first feature parameter associated with the radiation rays based on the imaging data. The at least one processor may further cause the system to monitor the medical device based on the first feature parameter associated with the radiation rays.

In some embodiments, the imaging data may include an intensity of radiation rays received by each of the plurality of detecting units and a position of each of the plurality of detecting units. The at least one processor may also cause the system to determine an intensity distribution of the radiation rays received by the plurality of detecting units based on the imaging data. The at least one processor may further cause the system to determine the first feature parameter based on the intensity distribution of the radiation rays.

In some embodiments, the at least one processor may also cause the system to obtain a first reference value corresponding to the first feature parameter. The at least one processor may further cause the system to compare the first reference value and the first feature parameter. The at least one processor may still further cause the system to determine whether the medical device is malfunctioning based on the comparison.

In some embodiments, the first feature parameter may include an intensity parameter relating to the radiation rays, and the first reference value may include a reference intensity. The at least one processor may also cause the system to determine that the medical device is malfunctioning in response to a determination that a difference between the intensity parameter relating to the radiation rays and the reference intensity exceeds a first threshold.

In some embodiments, the intensity parameter relating to the radiation rays may include at least one of a maximum intensity of radiation rays received by one of the plurality of detecting units, a minimum intensity of radiation rays received by one of the plurality of detecting units, or an average intensity of radiation rays received by the plurality of detecting units.

In some embodiments, the first feature parameter may include a parameter of a focus of the radiation rays. The at least one processor may also cause the system to determine that the medical device is malfunctioning in response to a determination that the parameter of the focus of the radiation rays exceeds a second threshold. The parameter of the focus of the radiation rays may include at least one of a position of the focus, a size of the focus, a shape of the focus, a vibration frequency of the focus, or a vibration amplitude of the focus.

In some embodiments, the at least one processor may also cause the system to estimate a service life of the anode target based on the parameter of the focus of the radiation rays.

In some embodiments, the at least one processor may also cause the system to adjust a parameter of a collimator of the medical device based on the parameter of the focus of the radiation rays. The parameter of the collimator may include at least one of a position of an opening of the collimator or a collimating width of the collimator.

In some embodiments, the at least one processor may also cause the system to increase the collimating width of the collimator in response to a determination that the vibration amplitude of the focus exceeds the second threshold.

In some embodiments, the at least one processor may also cause the system to adjust the position of the opening of the collimator based on the position of the focus and the vibration amplitude of the focus.

In some embodiments, the at least one processor may also cause the system to determine a second feature parameter associated with a component of the tube based on the first feature parameter. The at least one processor may further cause the system to determine whether the medical device is malfunctioning based on the second feature parameter.

In some embodiments, the at least one processor may also cause the system to obtain a second reference value corresponding to the second feature parameter. The at least one processor may further cause the system to compare the second reference value and the second feature parameter.

The at least one processor may still further cause the system to determine whether the medical device is malfunctioning based on the comparison.

In some embodiments, the at least one processor may also cause the system to determine that the medical device is malfunctioning in response to a determination that a difference between the second reference value and the second feature parameter exceeds a third threshold.

In some embodiments, the second feature parameter may include at least one of a rotation frequency of the anode target, a vibration amplitude of the anode target when rotating, or a rotation speed of the anode target.

In some embodiments, the first feature parameter may include a position of the focus, and the at least one processor may also cause the system to determine a change cycle of the position of the focus. The at least one processor may further cause the system to determine a vibration frequency of the focus based on the change cycle of the position of the focus. The at least one processor may still further cause the system to determine the rotation speed of the anode target based on the vibration frequency of the focus.

In some embodiments, the first feature parameter may include a position of the focus, and the at least one processor may also cause the system to determine a change cycle of the position of the focus. The at least one processor may further cause the system to determine a change of the position of the focus in the change cycle. The at least one processor may still further cause the system to determine the vibration amplitude the anode target when rotating based on the change of the position of the focus in the change cycle.

In some embodiments, the at least one processor may also cause the system to generate a malfunctioning alert in response to a determination that the medical device is malfunctioning.

According to another aspect of the present disclosure, a system for monitoring a medical device including a computer-readable storage medium storing executable instructions, and at least one processor in communication with the computer-readable storage medium. The medical device may include a tube configured to generate radiation rays and a detector configured to receive radiation rays emitted from the tube. When executing the executable instructions, the at least one processor may be configured to cause the system to obtain a vibration acceleration of the tube. The at least one processor may also cause the system to determine a rotation frequency of an anode target configured in the tube. the at least one processor may further cause the system to determine a service life of the anode target based on the rotation frequency of the anode target and a pre-set relationship between the service life of the anode target and the rotation frequency of the anode target.

According to still another aspect of the present disclosure, a method for monitoring a medical device implemented on a system having one or more processors and a computer-readable storage medium. The method may include obtaining imaging data acquired by the detector via detecting radiation rays emitted from the tube. The method may also include determining a first feature parameter associated with the radiation rays based on the imaging data. The method may further include monitoring the medical device based on the first feature parameter associated with the radiation rays.

In some embodiments, the method may also include determining a second feature parameter associated with a component of the tube based on the first feature parameter. The method may further include determining whether the medical device is malfunctioning based on the second feature parameter.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
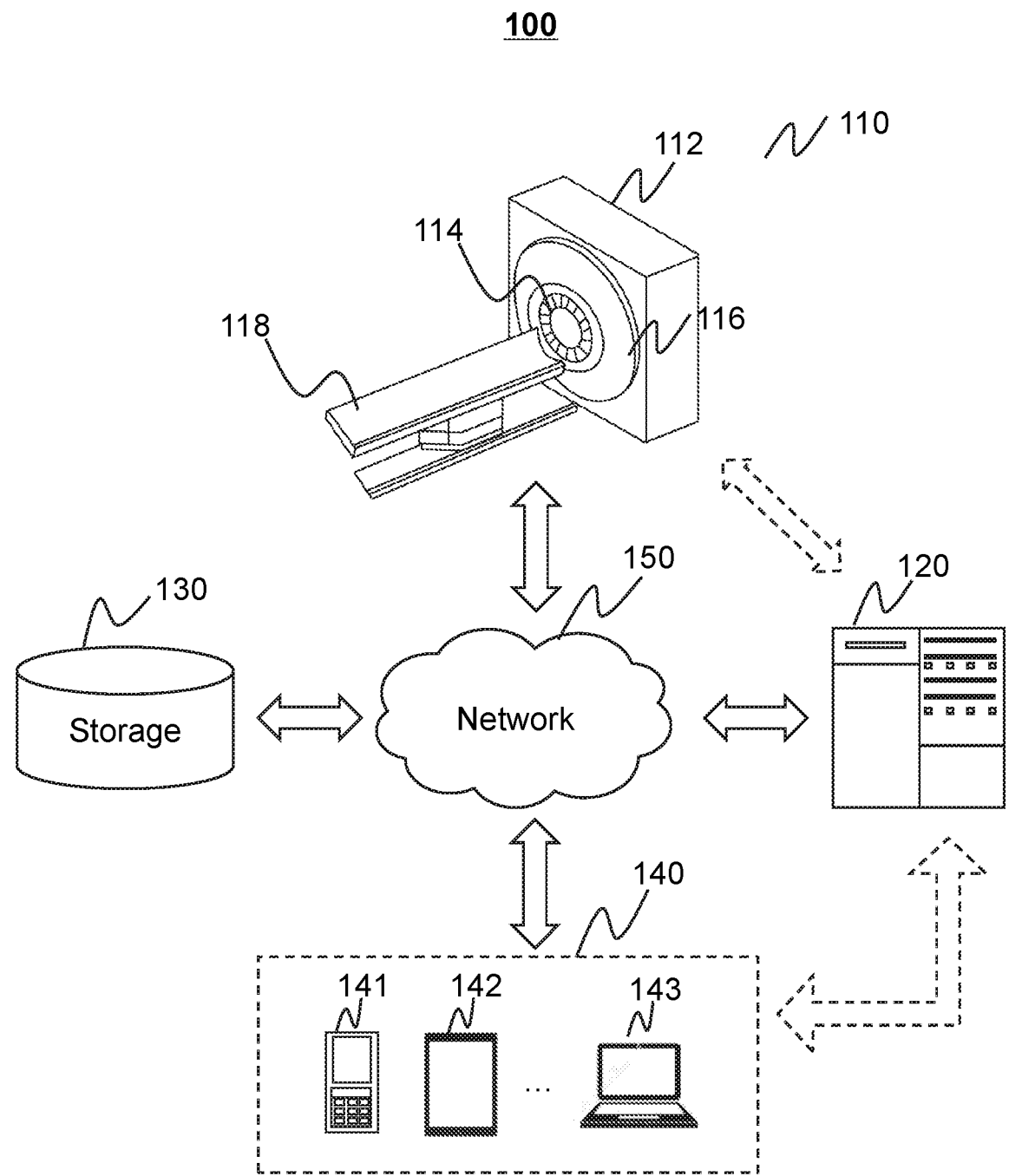
FIG. 1 is a schematic diagram illustrating a medical imaging system according to some embodiments of the present disclosure.

In order to illustrate the technical solutions related to the embodiments of the present disclosure, brief introduction of the drawings referred to in the description of the embodiments is provided below. Obviously, drawings described below are only some examples or embodiments of the present disclosure. Those having ordinary skills in the art, without further creative efforts, may apply the present disclosure to other similar scenarios according to these drawings. Unless stated otherwise or obvious from the context, the same reference numeral in the drawings refers to the same structure and operation.

As used in the disclosure and the appended claims, the singular forms "a," "an," and "the" include plural referents unless the content clearly dictates otherwise. It will be further understood that the terms "comprises," "comprising," "includes," and/or "including" when used in the disclosure, specify the presence of stated steps and elements, but do not preclude the presence or addition of one or more other steps and elements.

Some modules of the system may be referred to in various ways according to some embodiments of the present disclosure, however, any number of different modules may be used and operated in a client terminal and/or a server. These modules are intended to be illustrative, not intended to limit the scope of the present disclosure. Different modules may be used in different aspects of the system and method.

According to some embodiments of the present disclosure, flow charts are used to illustrate the operations performed by the system. It is to be expressly understood, the operations above or below may or may not be implemented in order. Conversely, the operations may be performed in inverted order, or simultaneously. Besides, one or more other operations may be added to the flowcharts, or one or more operations may be omitted from the flowchart.

Technical solutions of the embodiments of the present disclosure be described with reference to the drawings as described below. It is obvious that the described embodiments are not exhaustive and are not limiting. Other embodiments obtained, based on the embodiments set forth in the present disclosure, by those with ordinary skill in the art without any creative works are within the scope of the present disclosure.

Provided herein are systems and methods for monitoring a medical device. According to the present disclosure, the medical device may include a tube configured to generate radiation rays and a detector configured to receive radiation rays emitted from the tube. The tube may include an anode target and a filament. The detector may include a plurality of detecting units. The systems and the methods may obtain imaging data acquired by the detector via detecting radiation rays emitted from the tube. The systems and the methods may also determine a first feature parameter associated with the radiation rays based on the imaging data. The first feature parameter may include an intensity parameter associated with the radiation rays (e.g., a maximum intensity of radiation rays received by one of the plurality of detecting units, a minimum intensity of radiation rays received by one of the plurality of detecting units, an average intensity of radiation rays received by the plurality of detecting units), a parameter of a focus of the radiation rays (e.g., a position of the focus, a size of the focus, a shape of the focus, a vibration frequency of the focus, or a vibration amplitude of the focus), or the like, or any combination thereof. The systems and the methods may further monitor the medical device based on the first feature parameter associated with the radiation rays.

According to the present disclosure, the systems and the methods may obtain a vibration acceleration of the tube. The systems and methods may also determine a rotation frequency of an anode target configured in the tube. The systems and method may further determine a service life of the anode target based on the rotation frequency of the anode target and a pre-set relationship between the service life of the anode target and the rotation frequency of the anode target. Accordingly, the systems and methods may monitor one or more components of the medical device in real time as well as predict malfunctions in the medical device, which may improve the efficiency of the medical device and guarantee the safety of a user (e.g., operator).

FIG. 1 is a schematic diagram illustrating an exemplary imaging system 100 according to some embodiments of the present disclosure. As shown, the imaging system 100 may include a medical device 110, a processing device 120, a storage 130, one or more client terminal(s) 140, and a network 150. In some embodiments, the medical device 110, the processing device 120, the storage 130, and/or the client terminal(s) 140 may be connected to and/or communicate with each other via a wireless connection (e.g., the network 150), a wired connection, or a combination thereof. The connection between the components in the imaging system 100 may be variable. Merely by way of example, the medical device 110 may be connected to the processing device 120 through the network 150, as illustrated in FIG. 1. As another example, the medical device 110 may be connected to the processing device 120 directly. As a further example, the storage 130 may be connected to the processing device 120 through the network 150, as illustrated in FIG. 1, or connected to the processing device 120 directly. As still a further example, the client terminal(s) 140 may be connected to the processing device 120 through the network 150, as illustrated in FIG. 1, or connected to the processing device 120 directly.

The medical device 110 may be configured to scan an object using radiation rays and generate imaging data used to generate one or more images relating to the object. In some embodiments, the medical device 110 may transmit the imaging data to the processing device 120 for further processing (e.g., generating one or more images). In some embodiments, the imaging data and/or the one or more images associated with the object may be stored in the storage 130 and/or the processing device 120.

In some embodiments, the medical device 110 may be a computed tomography (CT) scanner, a suspended X-ray imaging device, a digital radiography (DR) scanner (e.g., a mobile digital X-ray imaging device), a digital subtraction angiography (DSA) scanner, a dynamic spatial reconstruction (DSR) scanner, an X-ray microscopy scanner, a multi-modality scanner, or the like, or a combination thereof. Exemplary multi-modality scanners may include a computed tomography-positron emission tomography (CT-PET) scanner, a computed tomography-magnetic resonance imaging (CT-MRI) scanner, etc. The object may be biological or non-biological. Merely by way of example, the object may include a patient, a man-made object, etc. As another example, the object may include a specific portion, organ, and/or tissue of a patient. For example, the object may include head, brain, neck, body, shoulder, arm, thorax, cardiac, stomach, blood vessel, soft tissue, knee, feet, or the like, or any combination thereof.

In some embodiments, the medical device 110 may include a gantry 112, a detector 114, a radiation source 116, and a table 118. A subject may be placed on the table 118 for scanning. In some embodiments, the radiation source 116 may include a tube (not shown in FIG. 1) and a collimator (not shown in FIG. 1). The tube may generate and/or emit radiation beams travelling toward the object. The radiation may include a particle ray, a photon ray, or the like, or a combination thereof. In some embodiments, the radiation may include a plurality of radiation particles (e.g., neutrons, protons, electron, μ-mesons, heavy ions), a plurality of radiation photons (e.g., X-ray, a γ-ray, ultraviolet, laser), or the like, or a combination thereof. In some embodiments, the tube may include an anode target and a filament. The filament may be configured to generate electrons to bombard the anode target. The anode target may be configured to generate the radiation rays (e.g., X-rays) when the electrons bombard the anode target. The collimator may be configured to control the irradiation region (i.e., radiation field) on the object. The collimator may also be configured to adjust the intensity and/or the number of the radiation beams that irradiate on the object.

The detector 114 may detect radiation beams. In some embodiments, the detector 114 may be configured to produce an analog electrical signal that represents the intensity of the received X-rays, including the attenuated beam, as it passes through the object. In some embodiments, the detector 114 may include a plurality of detecting units. The detecting units may include a scintillation detector (e.g., a cesium iodide detector), a gas detector, etc. The plurality of detecting units of the detector may be arranged in any suitable manner, for example, a single row, two rows, or another number of rows. More descriptions of components in the medical device 110 may be found elsewhere in the present disclosure (e.g., FIG. 2 and the descriptions thereof).

The processing device 120 may process data and/or information obtained from the medical device 110, the storage 130, and/or the client terminal(s) 140. For example, the processing device 120 may reconstruct an image relating to at least one part of an object (e.g., a tumor) based on imaging data collected by the medical device 110. As another example, the processing device 120 may determine feature parameters associated with the radiation rays emitted from the tube or one or more components of the medical device (e.g., the anode target). As a further example, the processing device 120 may determine whether the medical device is malfunctioning based on the determined feature parameter. As still another example, the processing device 120 may generate a malfunctioning alert in response to a determination that the medical device is malfunctioning. In some embodiments, the processing device 120 may be a single server or a server group. The server group may be centralized or distributed. In some embodiments, the processing device 120 may be local or remote. For example, the processing device 120 may access information and/or data from the medical device 110, the storage 130, and/or the client terminal(s) 140 via the network 150. As another example, the processing device 120 may be directly connected to the medical device 110, the client terminal(s) 140, and/or the storage 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof.

The storage 130 may store data, instructions, and/or any other information. In some embodiments, the storage 130 may store data obtained from the medical device 110, the processing device 120, and/or the client terminal(s) 140. For example, the storage 130 may store one or more scan parameters. As another example, the storage 130 may store the feature parameter associated with the radiation rays and/or one or more components of the medical device 110 (e.g., the anode target) determined by the processing device 120. As still an example, the storage 130 may store the malfunctioning information of the medical device 110. In some embodiments, the storage 130 may store data and/or instructions that the processing device 120 may execute or use to perform exemplary methods described in the present disclosure. In some embodiments, the storage 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 130 may be implemented on a cloud platform as described elsewhere in the disclosure.

In some embodiments, the storage 130 may be connected to the network 150 to communicate with one or more other components in the imaging system 100 (e.g., the processing device 120, the client terminal(s) 140). One or more components in the imaging system 100 may access the data or instructions stored in the storage 130 via the network 150. In some embodiments, the storage 130 may be part of the processing device 120.

The client terminal(s) 140 may be connected to and/or communicate with the medical device 110, the processing device 120, and/or the storage 130. For example, the client terminal(s) 140 may obtain image data acquired by the medical device 110 and transmit the image data to the processing device 120 to be processed. As another example, the client terminal(s) 140 may receive a malfunctioning alert in response to a determination that the medical device is malfunctioning. As still another example, a user may provide an input via a user interface implemented on the client terminal(s) 140. The input may include a request for determining whether the medical is malfunctioning. The input may also include one or more scan parameters, image construction parameters, reference values, etc., as described elsewhere in the present disclosure. In some embodiments, the client terminal(s) 140 may include a mobile device 141, a tablet computer 142, a laptop computer 143, or the like, or any combination thereof. For example, the mobile device 140-1 may include a mobile phone, a personal digital assistant (PDA), a gaming device, a navigation device, a point of sale (POS) device, a laptop, a tablet computer, a desktop, or the like, or any combination thereof. In some embodiments, the client terminal(s) 140 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the client terminal(s) 140 may be part of the processing device 120.

The network 150 may include any suitable network that can facilitate the exchange of information and/or data for the imaging system 100. In some embodiments, one or more components of the imaging system 100 (e.g., the medical device 110, the processing device 120, the storage 130, the client terminal(s) 140, etc.) may communicate information and/or data with one or more other components of the imaging system 100 via the network 150. For example, the processing device 120 may obtain image data from the medical device 110 via the network 150. As another example, the processing device 120 may obtain user instruction(s) from the client terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

Figure 2:
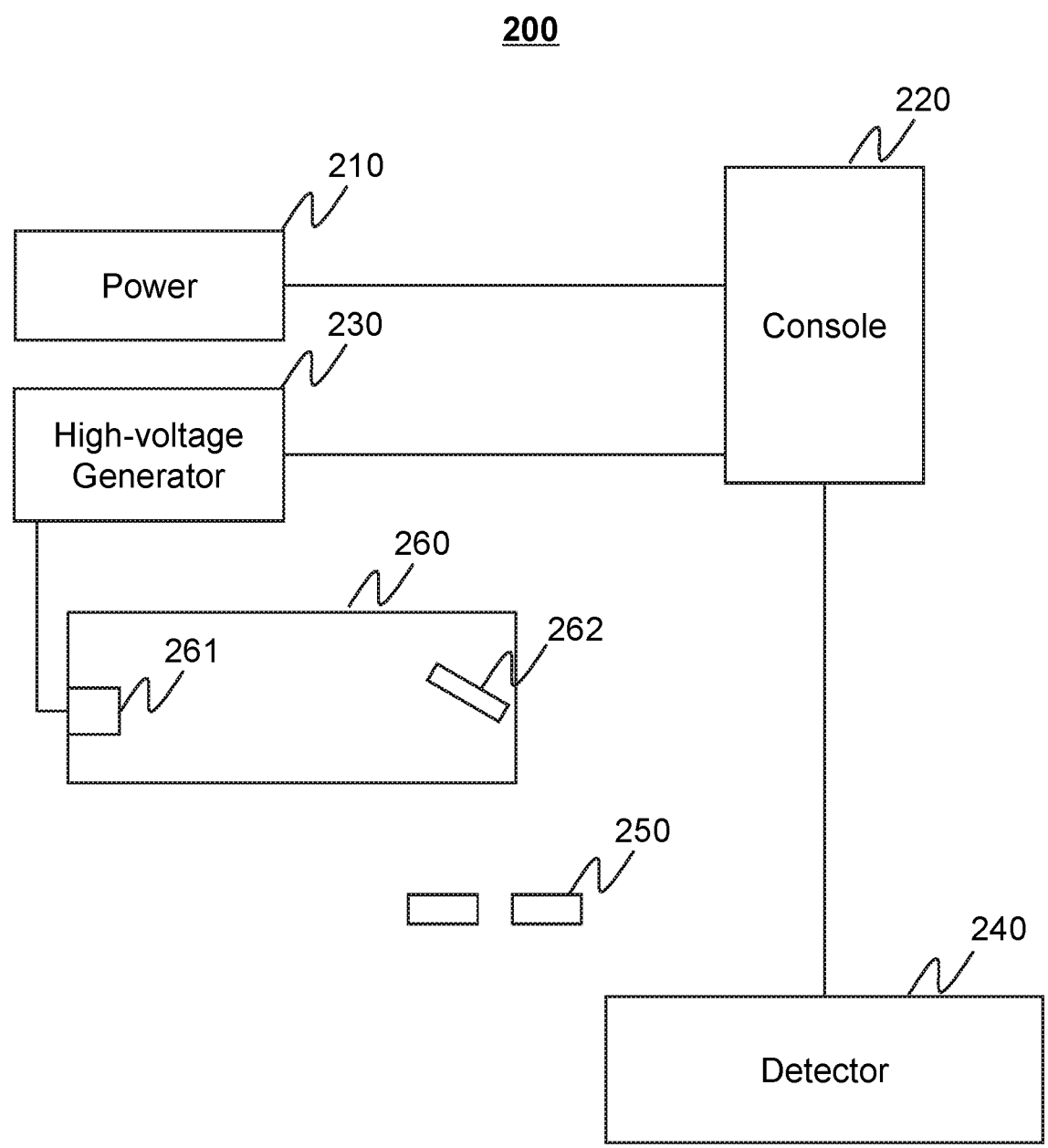
FIG. 2 is a schematic diagram illustrating an exemplary medical device according to some embodiments of the present disclosure.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage 130 may be a data storage including cloud computing platforms, such as public cloud, private cloud, community, and hybrid clouds, etc. As another example, the processing device 120 and the client terminal(s) 140 may be integrated into a console (e.g., the console 220 as shown in FIG. 2). However, those variations and modifications do not depart the scope of the present disclosure.

FIG. 2 is a schematic diagram illustrating an exemplary medical device 110 according to some embodiments of the present disclosure. As illustrated in the FIG. 2, the medical device 110 may include a power 210, a console 220, a high-voltage generator 230, a detector 240, a collimator 250, and a tube 260. In some embodiments, the power 210, the console 220, the high-voltage generator 230, the detector 240, the collimator 250, and/or the tube 260 may be connected to and/or communicate with each other via a wireless connection, a wired connection, or a combination thereof. The connection between the components of the medical device 110 may be variable. For example, the power 210 may be connected to the console 220 electrically. As another example, the console 220 may be connected to the detector 240 and the high-voltage generator 230 via a wireless connection (e.g., a network), a wired connection (e.g., a cable), or a combination thereof. As still another example, the high-voltage generator 230 may be electrically connected to the tube 260 via a cable.

The power 210 may be configured to power one or more components of the medical device 110, such as the console 220, the detector 240, the collimator 250, etc. The console 220 may be configured to control operation states of one or more components of the medical device 110, such as the high-voltage generator 230, the detector 240, and the tube 260. For example, the console 220 may control the high-voltage generator 230 to generate a high-voltage for the tube 260 according to an instruction input by a user or a default setting of the imaging system 100, such as scan parameters. As another example, the console 220 may control the detector 240 to collect image data. A user (e.g., an operator) may be in communication with the medical device 110 via the console. For example, a user may set scan parameters of the medical device 110 via the console 220. Exemplary scan parameters may include a tube current/voltage, an integration time of a detector, a size of the focus, a response of a detector, a response of a tube, a position of an opening of the collimator, a collimating width of the collimator, a field of view (FOV), etc.

The high-voltage generator 230 may be configured to generate a high-voltage and current for the tube 260. The tube 260 may include a filament 261 and an anode target 262. The high-voltage generated by the high-voltage generator 230 may trigger the filament 261 to emit a plurality of electrons to form an electron beam. The emitted electron beam may be impinged on a small area (i.e., the focus) on the anode target 262 to generate radiation beams (e.g., X-rays beams) consisting of high-energetic photons. The radiation beams may be collimated by the collimator 250 and project onto a surface of the detector 240. The detector 240 may detect the radiation beams collimated by the collimator 250 and generate data associated with the projection formed by the detected radiation beams (e.g., X-rays beams) as image data (also referred to as projection data). In some embodiments, the detector may include a plurality of detecting units. The plurality of detecting units of the detector may be arranged in any suitable manner, for example, a single row, two rows, or another number of rows. The image data (i.e., projection data) may be transmitted to the console 220 for further processing. For example, a processor in the console 220 may determine an intensity distribution of the radiation beams (or radiation rays) relative to the plurality of detecting units. The processor in the console 220 may further determine one or more feature parameters associated with the radiation beams, one or more parameters associated with one or more components of the medical device 110 (e.g., the anode target 262), etc. The processor in the console 220 may also determine whether the medical device 110 is malfunctioning based on the one or more feature parameters associated with the radiation beams, one or more parameters associated with one or more components of the medical device 110 (e.g., the anode target 262), etc.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the medical device 110 may further include a gantry configured to support one or more components of the medical device 110, such as, the detector 240, the collimator 250, and the tube 260.

Figure 3:
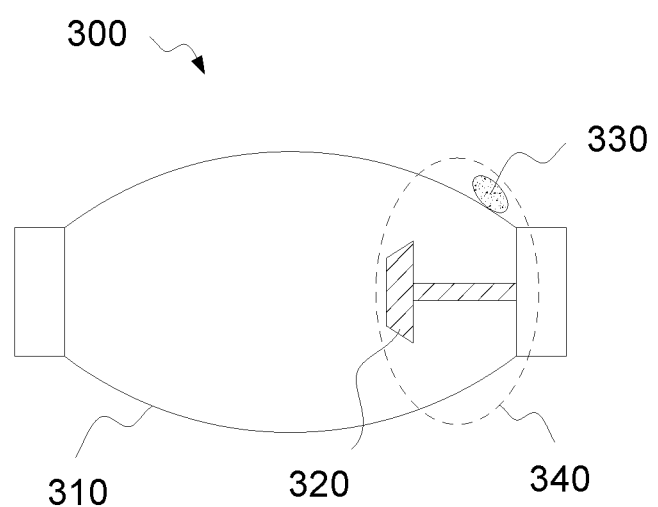
FIG. 3 is a schematic diagram illustrating an exemplary tube according to some embodiments of the present disclosure.

FIG. 3 is a schematic diagram illustrating an exemplary tube 300 according to some embodiments of the present disclosure. In some embodiments, the tube 300 may be an example of the tube 260 or a portion of the tube 260. As illustrated in FIG. 3, the tube 300 may include a shell 310, an anode target 320, and a sensor 330.

In some embodiments, the shell 310 may be configured to support at least one of a filament (not shown in FIG. 3), the anode target 320 and the sensor 330, and provide a certain condition for radiation beams generated by the filament, for example, a certain vacuum degree. The tube 300 may generate and/or emit radiation beams travelling toward an object as described elsewhere in the present disclosure (e.g., FIG. 2 and the descriptions thereof). In some embodiments, the rotating of the anode target 320 configured in the tube 300 may be driven by a motor, which may cause a vibration of the shell 310, etc. The sensor 330 may be fixedly mounted on the shell 310 of the tube 300 in a region (e.g., a region 340) adjacent to the anode target 320. The sensor 330 may obtain an acceleration signal of the shell 310 when the anode target 320 rotates. In some embodiments, the sensor 330 may be a vibration sensor (e.g., an acceleration sensor). The vibration acceleration of the tube 300 may be determined based on the acceleration signal. In some embodiments, a rotation frequency of the anode target 320 configured in the tube 300 may be determined based on the vibration acceleration of the tube 300. A service life of the anode target 320 may be determined based on the rotation frequency of the anode target 320 and a pre-set relationship between the service life of the anode target 320 and the rotation frequency of the anode target 320 as described elsewhere in the present disclosure (e.g., FIG. 15 and the descriptions thereof).

Figure 4:
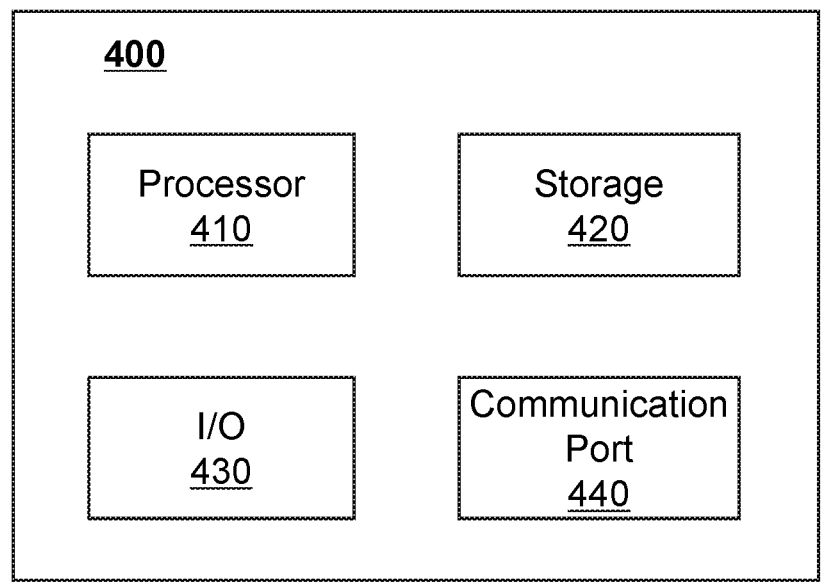
FIG. 4 is a schematic diagram illustrating exemplary hardware and/or software components of an exemplary computing device on which the processing device may be implemented according to some embodiments of the present disclosure.

FIG. 4 is a schematic diagram illustrating exemplary hardware and/or software components of an exemplary computing device 400 on which the processing device 120 may be implemented according to some embodiments of the present disclosure. As illustrated in FIG. 4, the computing device 400 may include a processor 410, a storage 420, an input/output (I/O) 430, and a communication port 440.

The processor 410 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 410 may process imaging data obtained from the medical device 110, the client terminal(s) 140, the storage 130, and/or any other component of the imaging system 100. In some embodiments, the processor 410 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combination thereof.

Merely for illustration, only one processor is described in the computing device 400. However, it should be noted that the computing device 400 in the present disclosure may also include multiple processors. Thus operations and/or method steps that are performed by one processor as described in the present disclosure may also be jointly or separately performed by the multiple processors. For example, if in the present disclosure the processor of the computing device 400 executes both process A and process B, it should be understood that process A and process B may also be performed by two or more different processors jointly or separately in the computing device 400 (e.g., a first processor executes process A and a second processor executes process B, or the first and second processors jointly execute processes A and B).

The storage 420 may store data/information obtained from the medical device 110, the client terminal(s) 140, the storage 130, and/or any other component of the imaging system 100. The storage 420 may be similar to the storage 130 described in connection with FIG. 1, and the detailed descriptions are not repeated here.

The I/O 430 may input and/or output signals, data, information, etc. In some embodiments, the I/O 430 may enable a user interaction with the processing device 120. In some embodiments, the I/O 430 may include an input device and an output device. Examples of the input device may include a keyboard, a mouse, a touchscreen, a microphone, a sound recording device, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touchscreen, or the like, or a combination thereof.

The communication port 440 may be connected to a network (e.g., the network 150) to facilitate data communications. The communication port 240 may establish connections between the processing device 120 and the medical device 110, the client terminal(s) 140, and/or the storage 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. In some embodiments, the communication port 440 may be and/or include a standardized communication port, such as RS232, RS485. In some embodiments, the communication port 440 may be a specially designed communication port. For example, the communication port 440 may be designed in accordance with the digital imaging and communications in medicine (DICOM) protocol.

Figure 5:
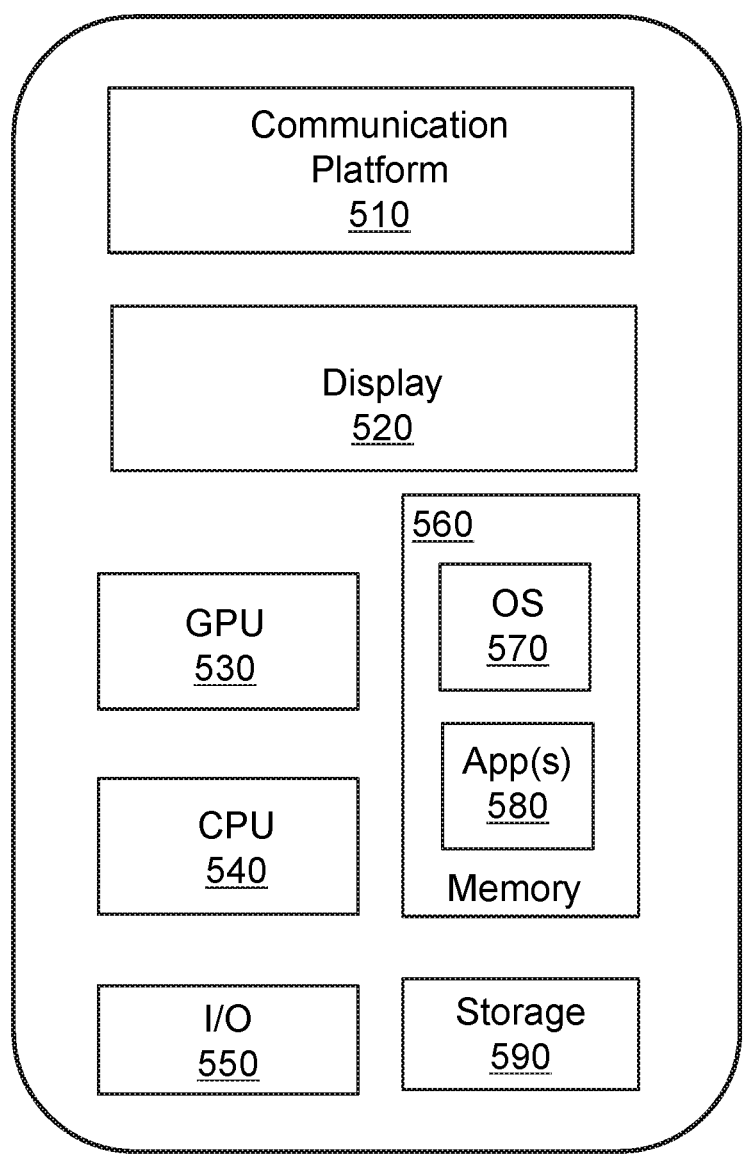
FIG. 5 is a schematic diagram illustrating exemplary hardware and/or software components of an exemplary mobile device on which the terminal(s) may be implemented according to some embodiments of the present disclosure.

FIG. 5 is a schematic diagram illustrating exemplary hardware and/or software components of an exemplary mobile device 500 on which the client terminal(s) 140 may be implemented according to some embodiments of the present disclosure.

As illustrated in FIG. 5, the mobile device 500 may include a communication platform 510, a display 520, a graphics processing unit (GPU) 530, a central processing unit (CPU) 540, an I/O 550, a memory 560, and a storage 590. In some embodiments, any other suitable component, including but not limited to a system bus or a controller (not shown), may also be included in the mobile device 500.

In some embodiments, the communication platform 510 may be configured to establish a connection between the mobile device 500 and other components of the imaging system 100, and enable data and/or signal to be transmitted between the mobile device 500 and other components of the imaging system 100. For example, the communication platform 510 may establish a wireless connection between the mobile device 500 and the medical device 110, and/or the processing device 120. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. The communication platform 510 may also enable the data and/or signal between the mobile device 500 and other components of the imaging system 100. For example, the communication platform 510 may transmit data and/or signals inputted by a user to other components of the imaging system 100. The inputted data and/or signals may include a user instruction. As another example, the communication platform 510 may receive data and/or signals transmitted from the processing device 120. The received data and/or signals may include imaging data acquired by a detector of the medical device 110.

In some embodiments, a mobile operating system (OS) 570 (e.g., iOS™ Android™, Windows Phone™, etc.) and one or more applications (App(s)) 580 may be loaded into the memory 560 from the storage 590 in order to be executed by the CPU 540. The applications 580 may include a browser or any other suitable mobile apps for receiving and rendering information respect to imaging process or other information from the processor 510. User interactions with the information stream may be achieved via the I/O 550 and provided to the processing device 120 and/or other components of the imaging system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or other type of work station or terminal device, although a computer may also act as a server if appropriately programmed. It is believed that those skilled in the art are familiar with the structure, programming and general operation of such computer equipment and as a result the drawings should be self-explanatory.

Figure 6:
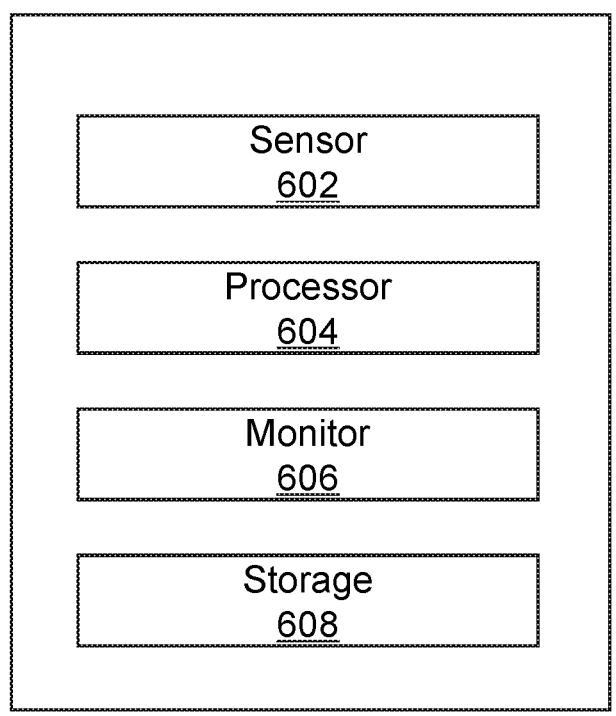
FIG. 6 is a schematic diagram illustrating an exemplary medical device according to some embodiments of the present disclosure.

FIG. 6 is a schematic diagram illustrating an exemplary medical device 600 according to some embodiments of the present disclosure. In some embodiments, the medical device 600 may be an example of the medical device 110 or a portion of the medical device 110. As illustrated in the FIG. 6, the medical device 600 may include a sensor 602, a processor 604, a monitor 606, and a storage 608. The medical device 600 may also include a tube, a detector, a collimator, etc., not shown in FIG. 6 as described elsewhere in the present disclosure (e.g., FIGS. 1-3 and the descriptions thereof). In some embodiments, the sensor 602, the processor 604, the monitor 606, and/or the storage 608 may be connected to and/or communicate with each other via a wireless connection, a wired connection, or a combination thereof. The connection between the components of the medical device 600 may be variable. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. In some embodiments, the components of the medical device 600 may be connected to and/or communicate with each other via a standardized communication protocol, for example, CANopen protocol, SPI protocol, RS485, etc. For example, the processor 604 may be connected to the sensor 602 to obtain a vibration acceleration of the tube. As another example, the monitor 606 may be connected to the processor 604 to obtain a rotation frequency of an anode target configured in the tube.

The sensor 602 may be configured to obtain an acceleration signal of a shell of the tube. In some embodiments, the sensor 602 may obtain the acceleration signal of the shell of the tube when an anode target configured in the tube rotates. The vibration acceleration of the tube may be determined based on the acceleration signal. The sensor 602 may be similar with or same as the sensor 330 as described in FIG. 3. For example, the sensor 602 may be mounted on the shell of the tube.

The processor 604 may determine a rotation frequency of an anode target configured in a tube. In some embodiments, the processor 604 may determine the rotation frequency of the anode target based on a vibration acceleration of the shell of the tube. In some embodiments, the processor 604 may perform one or more operations on the vibration acceleration of the tube to determine the rotation frequency of the anode target. For example, the processor 604 may perform a transform operation on the vibration acceleration of the tube to determine spectrum information associated with the rotation frequency of the anode target. Merely by ways of example, the transform operation may include a Fourier transform. The processor 604 may determine the rotation frequency of the anode target based on the spectrum information associated with the rotation frequency of the anode target.

The monitor 606 may determine a service life of an anode target. In some embodiments, the monitor 606 may determine the service life of the anode target based on the rotation frequency of the anode target and a pre-set relationship between the service life of the anode target and the rotation frequency of the anode target. In some embodiments, the pre-set relationship between the service life of the anode target and the rotation frequency of the anode target may be determined based on historical data associated with the service life of the anode target and the rotation frequency of the anode target. For example, the historical data associated with the service life of the anode target and the rotation frequency of the anode target may include the rotation frequencies of one or more reference anode targets and corresponding service lives, operating states, such as the rotation frequency of a reference anode target when the reference anode target retires and the corresponding service life. The pre-set relationship between the service life of the anode target and the rotation frequency of the anode target may be determined by performing a polynomial fitting or linear fitting based on the historical data associated with the service life of the anode target and the rotation frequency of the anode target.

In some embodiments, the pre-set relationship between the service life of the anode target and the rotation frequency of the anode target may be stored in a storage device (e.g., the storage 130, the storage 608) of the imaging system 100 or an external storage device. The monitor 606 may access the storage device and retrieve the pre-set relationship between the service life of the anode target and the rotation frequency of the anode target.

In some embodiments, the service life of the anode target may be transmitted to a client terminal (e.g., the client terminal 140) for display. The service life of the anode target may be presented in the client terminal in the form of text, audio, graph, video, or the like, or any combination thereof. For example, a text message, a voice message, or a video message including the service life of the anode target may be transmitted to the client terminal 140.

The monitor 606 may monitor operating states of one or more components of the medical device 600 and predict malfunctions in the medical device 600, which may avoid a sudden malfunction in the medical device 600 when the medical device 600 is in operation.

The storage 608 may store data, instructions, and/or any other information relating to the imaging system 100. In some embodiments, the storage 608 may store data obtained from the sensor 602, the processor 604, and/or the monitor 606. For example, the storage 608 may store an acceleration signal of a shell of a tube acquired by the sensor 602. As another example, the storage 608 may store a rotation frequency of an anode target determined by the processor 604. As still another example, the storage 608 may store a pre-set relationship between a service life of an anode target and a rotation frequency of an anode target. In some embodiments, the storage 608 may store data and/or instructions that the processor 604 and/or the monitor 606 may execute or use to perform exemplary methods described in the present disclosure. For example, the storage 608 may store instructions that the processor 604 may execute or use to determine a rotation frequency of an anode target. In some embodiments, the storage 608 may be connected to and/or to communicate with one or more other components in the medical device 600. One or more components in the medical device 600 may access the data or instructions stored in the storage 608. In some embodiments, the storage 608 may include a mass storage, a removable storage, a volatile read-and-write memory, a read-only memory (ROM), or the like, or any combination thereof as described elsewhere in the present disclosure.

Figure 7:
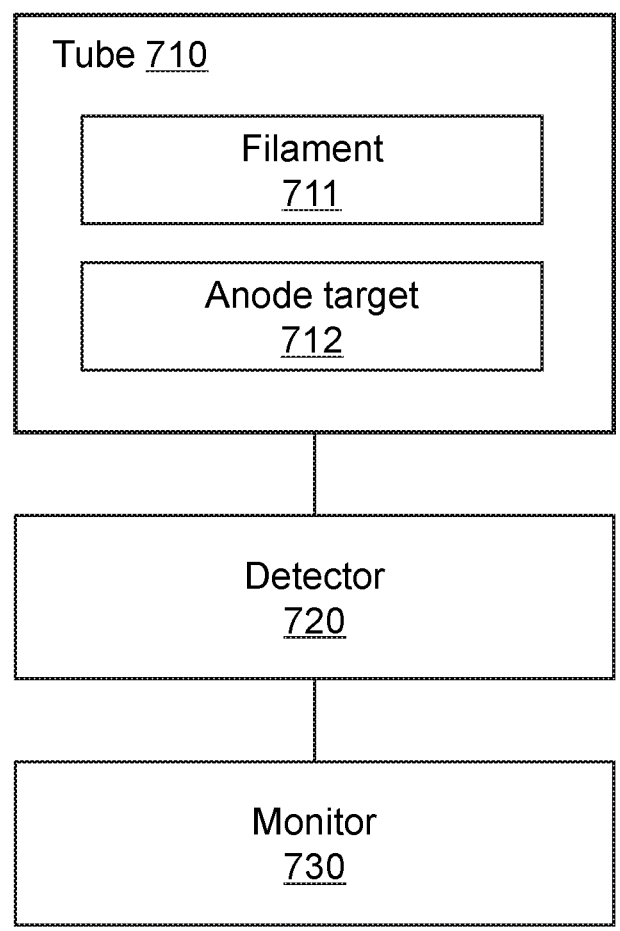
FIG. 7 is a schematic diagram illustrating an exemplary medical device according to some embodiments of the present disclosure.

FIG. 7 is a schematic diagram illustrating an exemplary medical device 700 according to some embodiments of the present disclosure. In some embodiments, the medical device 700 may be an example of the medical device 110 or a portion of the medical device 110.

As illustrated in the FIG. 7, the medical device 700 may include a tube 710, a detector 720, and a monitor 730. The tube 720 may include a filament 711 and an anode target 712. The filament 711 may generate a large number of electrons to form an electron beam when triggered by a high voltage. The emitted electron beam may be impinged on a small area on the anode target 712 to generate X-rays beams consisting of high-energetic photons. The small area on the anode target 712 may also be referred to as a focus of the X-rays beams. The focus of the X-rays beams may be defined by one or more parameters including the position of the focus, the size of the focus, the shape of the focus, the vibration frequency of the focus, the vibration amplitude of the focus, etc., as described elsewhere in the present disclosure. In some embodiments, the X-rays beams may be collimated by a collimator and project onto a surface of the detector 720. The detector 720 may receive radiation rays that projects or impinges on the detector 720 and generate imagining data, that may be also referred to as projection data. In some embodiments, the detector 720 may include a plurality of detecting units. The plurality of detecting units of the detector 720 may be arranged in any suitable manner, for example, a single row, two rows, or another number of rows. A parameter of radiation rays received by a detecting unit may include an intensity of the radiation rays and a position of the detecting unit. The projection data generated by the detecting unit may indicate the intensity of the radiation rays and the position of the detecting unit. The intensity of radiation rays received by different detecting units may be different or the same. The imaging data (e.g., the projection data) generated by the detector 720 may denote the intensity distribution of the radiation rays relative to the plurality of detecting units.

The monitor 730 may monitor the medical device 700 based on imaging data. In some embodiments, the monitor 730 may monitor one or more components of the medical device 700 (e.g., the filament 711, the anode target 712) based on the imaging data acquired by the detector 720. In some embodiments, the monitor 730 may include an acquisition module 831 and a processing module 832. The processing module 832 may include a calculating unit 8321, a parameter determination unit 8322, a reference value acquisition unit 8323, and a judging unit 8324. More descriptions regarding the monitor 730 may be found elsewhere in the present disclosure (e.g., FIG. 8 and the descriptions thereof).

Figure 8:
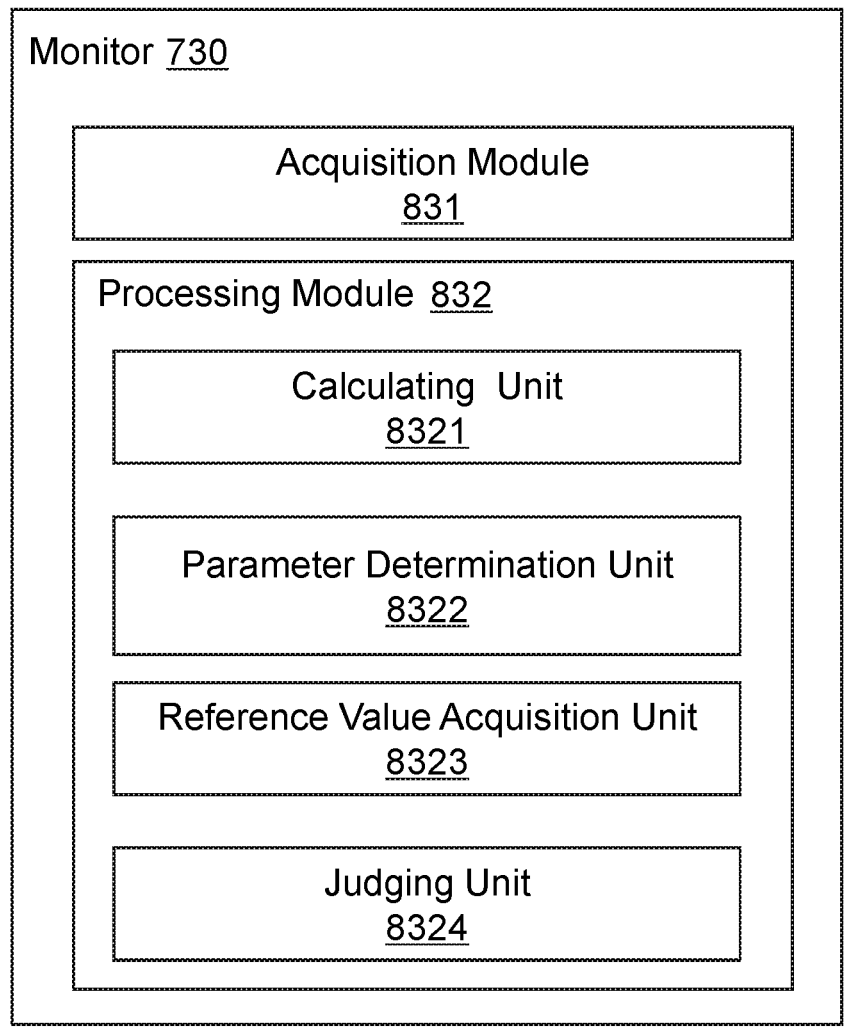
FIG. 8 is a schematic diagram illustrating an exemplary monitor according to some embodiments of the present disclosure.

FIG. 8 is a schematic diagram illustrating an exemplary monitor 730 according to some embodiments of the present disclosure. The monitor 730 may include an acquisition module 831 and a processing module 832. The processing module 832 may include a calculating unit 8321, a parameter determination unit 8322, a reference value acquisition unit 8323, and a judging unit 8324. The modules and/or the units may be hardware circuits of at least part of the monitor 730. The modules and/or the units may also be implemented as an application or set of instructions read and executed by the monitor 730. Further, the modules and/or the units may be any combination of the hardware circuits and the application/instructions. For example, the modules and/or the units may be the part of the monitor 730 when the monitor 730 is executing the application/set of instructions.

The acquisition module 831 may obtain imaging data acquired by a detector. The imaging data may be generated by the detector via detecting radiation rays emitted from a tube of a medical device. The imaging data (e.g., projection data) generated by the detector may indicate the intensity distribution of the radiation rays relative to a plurality of detecting units of the detector. In some embodiments, the acquisition module 831 may continuously or periodically obtain the imaging data from the medical device (e.g., the detector). For example, the acquisition module 831 may obtain the imaging data from the detector based on a Nyquist-Shannon sampling theorem. Additionally or alternatively, the detector of the medical device may transmit the imaging data to the storage (e.g., the storage 130, the storage 420) via the network 150 continuously or periodically. The acquisition module 831 may access the storage and retrieve the imaging data. In some embodiments, the acquisition module 831 may obtain an image (e.g., an X-ray image) associated with the imaging data from the medical device 110 or the storage 130. The acquisition module 831 may determine the imaging data (e.g., the projection data) by performing a transform operation (e.g., a Fourier transform).

In some embodiments, the acquisition module 831 may transfer the image data to other modules of the monitor 730 for further processing. For example, the acquisition module 831 may transfer the image data to the calculating unit 8321 for determining an intensity distribution of the radiation rays received by the plurality of detecting units. As another example, the acquisition module 831 may transfer the image data to the parameter determination unit 8322 for determining an intensity parameter relating to radiation rays.

The calculating unit 8321 may determine an intensity distribution of the radiation rays received by a plurality of detecting units of a detector. In some embodiments, the calculating unit 8321 may determine the intensity distribution of the radiation rays received by the plurality of detecting units based on an intensity of radiation rays received by each of the plurality of detecting units and a position of each of the plurality of detecting units.

In some embodiments, the calculating unit 8321 may transfer the intensity distribution of the radiation rays received by the plurality of detecting units to other modules of the monitor 730 for further processing. For example, the calculating unit 8321 may transfer the intensity distribution of the radiation rays received by the plurality of detecting units to the parameter determination unit 8322 for determining an intensity parameter relating to radiation rays.

The parameter determination unit 8322 may determine a first feature parameter associated with radiation rays. The first feature parameter may represent characteristics of the radiation rays, which may indicate operating states of one or more components of the medical device (e.g., the anode target, the filament, the collimator, etc.). In some embodiments, the first feature parameter may include an intensity parameter relating to the radiation rays received by the detector, a parameter of a focus of the radiation rays, or the like, or any combination thereof. The intensity parameter relating to the radiation rays may relate to the intensity of radiation rays received by at least one portion of the plurality of detecting units in the detector. The intensity parameter relating to the radiation rays may include a maximum intensity of radiation rays received by one of the plurality of detecting units, a minimum intensity of radiation rays received by one of the plurality of detecting units, an average intensity of the radiation rays received by the plurality of detecting units, or the like, or any combination thereof.

In some embodiments, the parameter determination unit 8322 may determine the intensity parameter relating to radiation rays (e.g., the maximum intensity, the minimum intensity, the average intensity, etc.) by analyzing the intensity distribution of the radiation rays. For example, the parameter determination unit 8322 may determine the maximum intensity of radiation rays by comparing intensities of radiation rays with each other in the intensity distribution of the radiation rays. In some embodiments, the parameter determination unit 8322 may determine the parameter of the focus based on the intensity distribution of the radiation rays. For example, the parameter determination unit 8322 may determine a position of focus based on the maximum of radiation rays received by the detector. More descriptions of the intensity distribution of the radiation rays may be found elsewhere in the present disclosure (e.g., FIGS. 11, 16-20, and the descriptions thereof).

In some embodiments, the parameter determination unit 8322 may determine a second feature parameter associated with a component of a tube based on the first feature parameter. The second feature parameter may include a rotation frequency of the anode target, a vibration amplitude of the anode target when rotating, a rotation speed of the anode target, or the like, or any combination thereof. For example, the parameter determination unit 8322 may determine the rotation speed of the anode target of the tube based on a vibration frequency of the focus as described in connection with FIG. 13 and the descriptions thereof. As another example, the parameter determination unit 8322 may determine the vibration amplitude of the anode target when rotating based on the vibration amplitude of the focus as described in connection with FIG. 14 and the descriptions thereof.

In some embodiments, the parameter determination unit 8322 may transfer the first feature parameter and/or the second feature parameter to other modules of the monitor 730 for further processing. For example, the parameter determination unit 8322 may transfer the first feature parameter and/or the second feature parameter to the judging unit 8324 for monitoring one or more components of the medical device.

The reference value acquisition unit 8323 may obtain a reference value corresponding to a feature parameter (e.g., a first feature parameter, a second feature parameter). As used herein, a reference value corresponding to a specific feature parameter may refer to a desired value of the specific feature parameter when the medical device is functioning well. The reference value corresponding to a specific feature parameter may be an empirical value determined based on statistical analysis of data collected from a well-functioning medical device. In some embodiments, the reference value acquisition unit 8323 may obtain the reference value from one or more components of the imaging system 100, such as a storage device (e.g., the storage 130), or a terminal (e.g., a client terminal 140). In some embodiments, the reference value acquisition unit 8323 may obtain the reference value from an external data source or storage connected to the imaging system 100 via the network 150.

In some embodiments, the reference value acquisition unit 8323 may transfer the reference value to other modules of the monitor 730 for further processing. For example, the reference value acquisition unit 8323 may transfer the reference value to the judging unit 8324 for monitoring one or more components of the medical device.

The judging unit 8324 may determine whether the medical device is malfunctioning based on a feature parameter (e.g., a first feature parameter, a second feature parameter) and a corresponding reference value.

The judging unit 8324 may determine whether the medical device is malfunctioning based on the first feature parameter (e.g., the intensity parameter associated with the radiation rays, the vibration frequency of the focus, the vibration amplitude of the focus) and a first reference value corresponding to the first feature parameter. For example, the judging unit 8324 may determine whether the medical device is malfunctioning based on a difference between the first feature parameter and the first reference value. The judging unit 8324 may determine whether the difference between the first feature parameter and the first reference value exceeds a first threshold. In response to a determination that the difference between the first feature parameter and the first reference value exceeds the first threshold, the judging unit 8324 may determine that the medical device is malfunctioning. As another example, the judging unit 8324 may determine whether the first feature parameter exceeds (or less than) the first reference value. In response to a determination that the first feature parameter exceeds (or less than) the first reference value, the judging unit 8324 may determine that the medical device is malfunctioning. In other words, the first feature parameter and the medical device is abnormal. The first threshold and/or the first reference value may be preset manually by a user, or may be determined by one or more components of the imaging system 100 according to different situations.

The judging unit 8324 may determine whether the medical device is malfunctioning based on the second feature parameter (e.g., the rotation speed of the anode target, the vibration amplitude of the anode target when rotating) and a second reference value corresponding to the second feature parameter. For example, the judging unit 8324 may determine whether the second feature parameter exceeds (or lowers than) the second reference value. In response to a determination that the second feature parameter exceeds (or lowers than) the second reference value, the judging unit 8324 may determine that the medical device is malfunctioning. In other words, the second feature parameter and the medical device is abnormal. More descriptions regarding the monitoring of the medical device based on the second feature parameter may be found elsewhere in the present disclosure (e.g., FIG. 10 and the descriptions thereof).

In some embodiments, the judging unit 8324 may determine malfunctioning information of the medical device based on the first feature parameter and/or the second feature parameter. The malfunctioning information may include the type of a malfunction, a malfunctioning component, a recommendation for eliminating the malfunction, or the like, or any combination thereof.

In some embodiments, the judging unit 8324 may generate a malfunctioning alert in response to a determination that the medical device is malfunctioning. In some embodiments, the malfunctioning alert may include a text alert, an audio alert, a certain graph, a light alert, a vibration alert, or the like, or any combination thereof. In some embodiments, the malfunctioning alert may further include the malfunctioning information, for example, the type of the malfunction, the malfunctioning module, the recommendation for eliminating malfunction, etc., as described in operation 906.

In some embodiments, the judging unit 8324 may transfer the malfunctioning information of the medical device and/or the malfunctioning alert to other modules of the monitor 730. For example, the judging unit 8324 may transmit a signal including the malfunctioning alert to the client terminal 140. The judging unit 8324 may transmit the signal using a text message, a voice message, or a video message including the malfunctioning information. The signal may be also configured to cause the client terminal to display the malfunctioning alert on a visual interface of the client terminal 140 via the network 150.

It should be noted that the above description of the monitor 730 is merely provided for the purposes of illustration, and not intended to limit the scope of the present disclosure. For persons having ordinary skills in the art, multiple variations and modifications may be made under the teachings of the present disclosure. For example, the monitor 730 may further include a storage module facilitating data storage. As another example, the calculating unit 8321 and the parameter determination unit 8322 may be merged into a single unit. However, those variations and modifications do not depart from the scope of the present disclosure.

Figure 9:
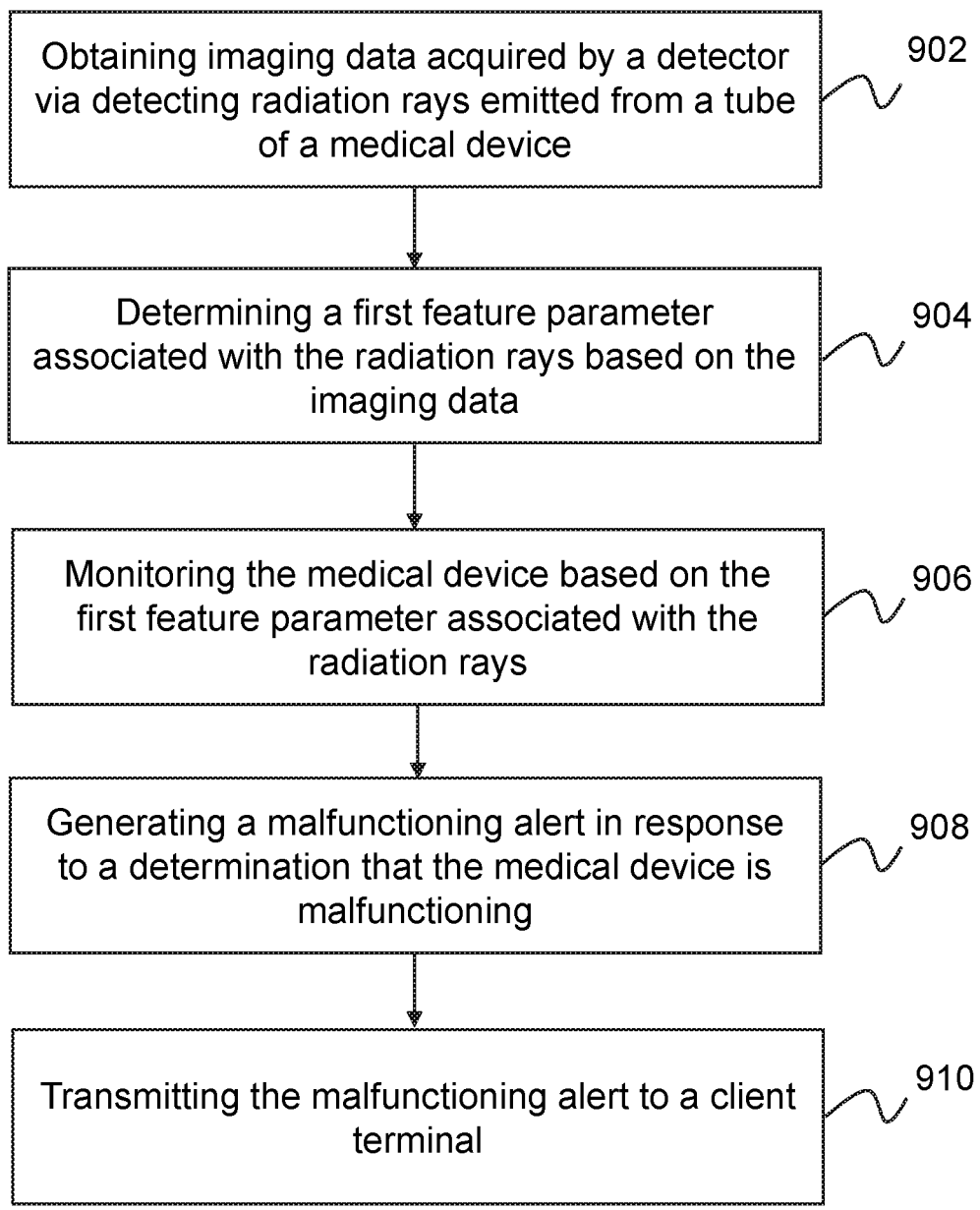
FIG. 9 is a flowchart illustrating an exemplary process for monitoring a medical device according to some embodiments of the present disclosure.

FIG. 9 is a flowchart illustrating an exemplary process 900 for monitoring a medical device according to some embodiments of the present disclosure. In some embodiments, the process 900 may be implemented in the imaging system 100 illustrated in FIG. 1. For example, the process 900 may be stored in the storage 130 and/or the storage (e.g., the storage 420, the storage 490) as a form of instructions, and invoked and/or executed by the processing engine 120 (e.g., the processor 410 of the computing device 400 as illustrated in FIG. 3, the CPU 440 of the mobile device 500 as illustrated in FIG. 4).

In 902, imaging data acquired by a detector via detecting radiation rays emitted from a tube of a medical device may be obtained. Operation 902 may be performed by the acquisition module 831. The tube of the medical device (e.g., an X-ray imaging device, a CT device, etc.) may generate and/or emit radiation rays travelling toward an object to be scanned as described elsewhere in the present disclosure. The imaging data (e.g., projection data) generated by the detector may indicate the intensity distribution of the radiation rays relative to a plurality of detecting units of the detector. In some embodiments, the acquisition module 831 may continuously or periodically obtain the imaging data from the medical device (e.g., the detector).

In some embodiments, the acquisition module 831 may continuously or periodically obtain the imaging data from the medical device (e.g., the detector). For example, the acquisition module 831 may obtain the imaging data from the detector based on a Nyquist-Shannon sampling theorem. The sampling frequency of the imaging data may be greater than a rotation speed of the anode target of the tube. For example, the sampling frequency of the imaging data may be greater than twice the rotation speed of the anode target. Additionally or alternatively, the detector of the medical device may transmit the imaging data to the storage (e.g., the storage 130, the storage 420) via the network 150 continuously or periodically. The acquisition module 831 may access the storage and retrieve the imaging data. In some embodiments, the acquisition module 831 may obtain an image (e.g., an X-ray image) associated with the imaging data from the medical device 110 or the storage 130. The acquisition module 831 may determine the imaging data (e.g., the projection data) by performing a transform operation (e.g., a Fourier transform).

In 904, a first feature parameter associated with the radiation rays may be determined based on the imaging data. Operation 904 may be performed by the calculating unit 8321 and/or the parameter determination unit 8322.

The first feature parameter may represent characteristics of the radiation rays, which may indicate operating states of one or more components of the medical device (e.g., the anode target, the filament, the collimator, etc.). In some embodiments, the first feature parameter may include an intensity parameter relating to the radiation rays received by the detector, a parameter of a focus of the radiation rays, or the like, or any combination thereof. The intensity parameter relating to the radiation rays may relate to the intensity of radiation rays received by at least one portion of the plurality of detecting units in the detector. The intensity parameter relating to the radiation rays may include a maximum intensity of radiation rays received by one of the plurality of detecting units, a minimum intensity of radiation rays received by one of the plurality of detecting units, an average intensity of the radiation rays received by the plurality of detecting units, or the like, or any combination thereof. As used herein, the maximum intensity of radiation rays received by one of the plurality of detecting units may refer to a maximum value of the intensity of radiation rays received by each of the plurality of detecting units. The minimum intensity of radiation rays received by one of the plurality of detecting units may refer to a minimum value of the intensity of radiation rays received by each of the plurality of detecting units. The average intensity of the radiation rays received by the plurality of detecting units may refer to an average value of the intensity of radiation rays received by each of the plurality of detecting units. The parameter of the focus of the radiation rays may include the position of the focus, the size of the focus, the shape of the focus, the vibration frequency of the focus, the vibration amplitude of the focus, etc., as described elsewhere in the present disclosure. As used herein, the position of the focus may be denoted by the position of a detecting unit which receives a maximum intensity of radiation rays.

The parameter determination unit 8322 may determine the first feature parameter based on the intensity distribution of the radiation rays. The imaging data (i.e., projection data) may indicate the intensity distribution of the radiation rays received by the plurality of detecting units. In some embodiments, the parameter determination unit 8322 may determine the intensity parameter relating to radiation rays (e.g., the maximum intensity, the minimum intensity, the average intensity, etc.) by analyzing the intensity distribution of the radiation rays. For example, the parameter determination unit 8322 may determine the maximum intensity of radiation rays by comparing intensities of radiation rays with each other in the intensity distribution of the radiation rays. In some embodiments, the parameter determination unit 8322 may determine the parameter of the focus based on the intensity distribution of the radiation rays. For example, the parameter determination unit 8322 may determine a position of focus based on the maximum of radiation rays received by the detector. More descriptions for determining the parameters associated with the radiation rays may be found elsewhere in the present disclosure (e.g., FIGS. 11-12, 17-20, and the descriptions thereof).

In 906, the medical device may be monitored based on the first feature parameter associated with the radiation rays. Operation 906 may be performed by the reference value acquisition unit 8323 and/or the judging unit 8324.

In some embodiments, the judging unit 8324 may determine whether the medical device is malfunctioning based on the first feature parameter (e.g., the intensity parameter associated with the radiation rays, the vibration frequency of the focus, the vibration amplitude of the focus, etc.) and a first reference value corresponding to the first feature parameter. For example, the judging unit 8324 may determine whether the medical device is malfunctioning based on a difference between the first feature parameter and the first reference value. The judging unit 8324 may determine whether the difference between the first feature parameter and the first reference value exceeds a first threshold. In response to a determination that the difference between the first feature parameter and the first reference value exceeds the first threshold, the judging unit 8324 may determine that the medical device is malfunctioning. As another example, the judging unit 8324 may determine whether the first feature parameter exceeds (or less than) the first reference value. In response to a determination that the first feature parameter exceeds (or less than) the first reference value, the judging unit 8324 may determine that the medical device is malfunctioning. In other words, the first feature parameter and the medical device is abnormal. The first threshold and/or the first reference value may be preset manually by a user, or may be determined by one or more components of the imaging system 100 according to different situations.

In some embodiments, the judging unit 8324 may monitor the medical device based on a second feature parameter associated with one or more components of the tube (e.g., the anode target, the filament). The second feature parameter may include a rotation frequency of the anode target, a vibration amplitude of the anode target when rotating, a rotation speed of the anode target, a service life of the anode target, or the like, or any combination thereof. In some embodiments, the parameter determination unit 8322 may determine the second feature parameter associated with a component of the tube based on the first feature parameter. For example, the parameter determination unit 8322 may determine the rotation speed of the anode target based on the vibration frequency of the focus. As another example, the parameter determination unit 8322 may determine the vibration amplitude of the anode target when rotating based on the vibration amplitude of the focus.

The judging unit 8324 may determine whether the medical device is malfunctioning based on the second feature parameter (e.g., the rotation speed of the anode target, the vibration amplitude of the anode target when rotating, etc.) and a second reference value corresponding to the second feature parameter. For example, the judging unit 8324 may determine whether the second feature parameter exceeds (or lowers than) the second reference value. In response to a determination that the second feature parameter exceeds (or lowers than) the second reference value, the judging unit 8324 may determine that the medical device is malfunctioning. In other words, the second feature parameter and the medical device is abnormal. More descriptions regarding the monitoring of the medical device based on the second feature parameter may be found elsewhere in the present disclosure (e.g., FIGS. 10, 13, and 14 and the descriptions thereof).

In some embodiments, the judging unit 8324 may determine malfunctioning information of the medical device based on the first feature parameter and/or the second feature parameter. The malfunctioning information may include the type of a malfunction, a malfunctioning component, a recommendation for eliminating the malfunction, or the like, or any combination thereof. For example, if the judging unit 8324 determines that the intensity distribution of the radiation rays received by the plurality of detecting units is consistent (or normal), the size of the focus is normal, and the position of the focus is abnormal, it may indicate that there is a malfunction in an electric field control of the medical device. As another example, if the judging unit 8324 determines that the intensity distribution of the radiation rays received by the plurality of detecting units is inconsistent (or abnormal), the size of the focus is normal, and the position of the focus is abnormal, it may indicate that there is a high-voltage output malfunction (e.g., a malfunction in the high-voltage generator 230) in the medical device. As still another example, if the judging unit 8324 determines that the intensity distribution of the radiation rays received by the plurality of detecting units is inconsistent (or normal), the size of the focus and the position of the focus are abnormal, it may indicate that there is a high-voltage output malfunction (e.g., a malfunction in the high-voltage generator 230) or a tube malfunction in the medical device. As still another example, if the judging unit 8324 determines that characteristic of the focus (denoted by the parameter of the focus) is unstable, it may indicate that a focus control module in the medical device is malfunctioning. In some embodiments, the judging unit 8324 may analyze the malfunctioning components of the medical device based on logs and/or feedback parameters.

In some embodiment, the judging unit 8324 may determine whether the filament of the tube is malfunctioning based on the intensity distribution of the radiation rays received by the plurality of detecting units. For example, if the filament of the tube is not malfunctioning, the intensity of radiation rays received by the plurality of detecting units may be evenly distributed according to a certain rule, also referred to as the intensity distribution of the radiation rays may be consistent. If the filament of the tube is malfunctioning, the intensity distribution of the radiation rays received by the plurality of detecting units may be abnormal or inconsistent. In some embodiments, if a voltage output of a high-voltage generator of the medical device is abnormal or malfunctioning, such as lower than a reference voltage value, the effective electron density emitted by the filament of the tube may be lower than a reference density value. Accordingly, the intensity of the radiation rays and the shape of the focus may be abnormal.

In some embodiments, the processing module 832 may adjust one or more parameters of one or more components of the medical device based on the first feature parameter and/or the second feature parameter. In some embodiments, the processing module 832 may adjust the parameter of a collimator of the medical device based on the parameter of the focus of the radiation rays. The parameter of the collimator may include a position of an opening of the collimator, a collimating width of the collimator, or the like, or any combination thereof. For example, the processing module 832 may increase the collimating width of the collimator in response to a determination that the vibration amplitude of the focus exceeds the second threshold. As another example, the processing module 832 may adjust the position of the opening of the collimator based on the position of the focus and the vibration amplitude of the focus.

In some embodiments, the processing module 832 may estimate a service life of one or more components (e.g., the anode target) of the medical device. For example, the processing module 832 may determine the service life of the anode target based on the rotation speed of the anode target and a pre-set relationship between the service life of the anode target and the rotation speed of the anode target as described elsewhere in the present disclosure (e.g., FIG. 13 and the descriptions thereof).

In 908, in response to a determination that the medical device is malfunctioning, a malfunctioning alert may be generated. Operation 908 may be performed by the judging unit 8324. In some embodiments, the malfunctioning alert may include a text alert, an audio alert, a certain graph, a light alert, a vibration alert, or the like, or any combination thereof. In some embodiments, the malfunctioning alert may further include the malfunctioning information, for example, the type of the malfunction, the malfunctioning module, the recommendation for eliminating malfunction, etc., as described in operation 906.

In 910, the malfunctioning alert may be transmitted to a client terminal. Operation 910 may be performed by the processing module 832. In some embodiments, the processing module 832 may transmit a signal including the malfunctioning alert to the client terminal 140. The processing module 832 may transmit the signal using a text message, a voice message, or a video message including the malfunctioning information. The signal may also be configured to cause the client terminal to display the malfunctioning alert on a visual interface of the client terminal 140 via the network 150.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted. For example, operation 908 and operation 910 may be merged into a single operation. As another example, operation 908 and/or operation 910 may be omitted. As still another example, a pre-processing operation may be added before operation 904. The image data may be pre-processed (e.g., filtered, de-noised, classified, or sorted) by the processing module 832.

Figure 10:
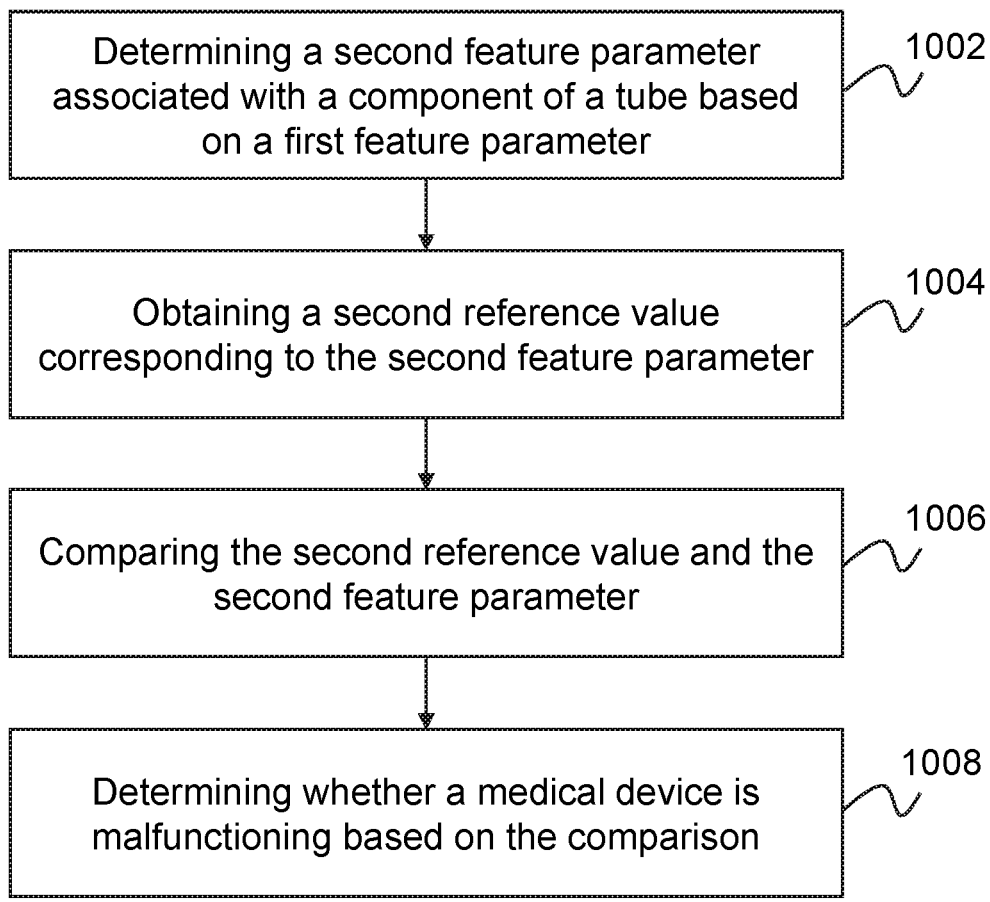
FIG. 10 is a flowchart illustrating an exemplary process for monitoring a medical device according to some embodiments of the present disclosure.

FIG. 10 is a flowchart illustrating an exemplary process 1000 for monitoring a medical device according to some embodiments of the present disclosure. In some embodiments, the process 1000 may be implemented in the imaging system 100 illustrated in FIG. 1. For example, the process 1000 may be stored in the storage 130 and/or the storage (e.g., the storage 420, the storage 490) as a form of instructions, and invoked and/or executed by the processing engine 120 (e.g., the processor 410 of the computing device 400 as illustrated in FIG. 3, the CPU 440 of the mobile device 500 as illustrated in FIG. 4). Operation 906 may be performed according to process 1000.

In 1002, a second feature parameter associated with a component of a tube may be determined based on a first feature parameter associated with radiation rays. Operation 1002 may be performed by the calculating unit 8321 and/or the parameter determination unit 8322. The tube may include an anode target as described elsewhere in the present disclosure (e.g., FIGS. 2, 7 and 9, and the descriptions thereof). The first feature parameter associated with the radiation rays may include an intensity parameter relating to the radiation rays received by a detector, a parameter of a focus of the radiation rays, etc., as described elsewhere in the present disclosure (e.g., FIG. 9 and the descriptions thereof). For example, the parameter of the focus of the radiation rays may include the position of the focus, the size of the focus, the shape of the focus, the vibration frequency of the focus, the vibration amplitude of the focus, etc. The second feature parameter may include a rotation frequency of the anode target, a vibration amplitude of the anode target when rotating, a rotation speed of the anode target, or the like, or any combination thereof.

In some embodiments, the processing module 832 may determine the rotation speed of the anode target of the tube based on a vibration frequency of the focus. For example, the processing module 832 may determine a change cycle of the position of the focus based on the position of the focus. The processing module 832 may also determine a vibration frequency of the focus based on the change cycle of the position of the focus. Further, the processing module 832 may determine the rotation speed of the anode target based on the vibration frequency of the focus. In some embodiments, the processing module 832 may further determine the rotation frequency of the anode target based on the rotation speed of the anode target. More descriptions regarding the determination of the rotation speed of the anode target may be found elsewhere on the present disclosure (e.g. FIG. 13 and the descriptions thereof).

In some embodiments, the processing module 832 may determine the vibration amplitude of the anode target when rotating based on the vibration amplitude of the focus. For example, the processing module 832 may determine a change cycle of the position of the focus based on the position of the focus. The processing module 832 may also determine a change of the position of the focus in the change cycle. Further, the processing module 832 may determine the vibration amplitude of the focus based on the change of the position of the focus in the change cycle and determine the vibration amplitude of the anode target when rotating based on the vibration amplitude of the focus. More descriptions regarding the determination of the vibration amplitude of the anode target when rotating may be found elsewhere on the present disclosure (e.g. FIG. 14 and the descriptions thereof).

In 1004, a second reference value corresponding to the second feature parameter may be obtained. Operation 1004 may be performed by the reference value acquisition unit 8323.

As used herein, a reference value corresponding to a specific second feature parameter may refer to a desired value of the specific second feature parameter when the medical device is functioning well. The reference value specific corresponding to a specific second feature parameter may be an empirical value determined based on statistical analysis of data collected from a well-functioning medical device. In some embodiments, the reference value acquisition unit 8323 may obtain the second reference value from one or more components of the imaging system 100, such as a storage device (e.g., the storage 130), or a terminal (e.g., a client terminal 140). In some embodiments, the reference value acquisition unit 8323 may obtain the second reference value from an external data source or storage connected to the imaging system 100 via the network 150.

In 1006, the second reference value and the second feature parameter may be compared. Operation 1006 may be performed by the judging unit 8324.

In some embodiments, the judging unit 8324 may compare the second reference value and the second feature parameter by comparing a difference between the second reference value and the second feature parameter with a threshold. For example, the judging unit 8324 may determine the difference by subtracting the second reference value (or the second feature parameter) from the second feature parameter (or the second reference value). As another example, the judging unit 8324 may determine the difference by dividing the second reference value (or the second feature parameter) by the second feature parameter (or the second reference value). The judging unit 8324 may compare the second reference value and the second feature parameter by determining whether the difference between the second reference value and the second feature parameter exceeds the threshold. In some embodiments, the judging unit 8324 may compare the second reference value and the second feature parameter by determining whether the second feature parameter exceeds (or lowers than) the second reference value. The threshold may be preset manually by a user, or may be determined by one or more components of the imaging system 100 according to different situations.

In 1008, a determination may be made as to whether the medical device is malfunctioning based on the comparison. Operation 1008 may be performed by the judging unit 8324.

In some embodiments, the judging unit 8324 may determine whether the medical device is malfunctioning based on the difference between the second reference value and the second feature parameter and the threshold. For example, in response to a determination that the difference between the second reference value and the second feature parameter (e.g., a vibration amplitude of the anode target when rotating) exceeds the threshold, the judging unit 8324 may determine that the medical device is malfunctioning. In response to a determination that the difference between the second reference value and the second feature parameter does not exceed the third threshold, the judging unit 8324 may determine that the medical device is not malfunctioning. As another example, in response to a determination that the second feature parameter (e.g., a rotation speed of the anode target) exceeds (or lowers than) the second reference value, the judging unit 8324 may determine that the medical device is malfunctioning.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 11:
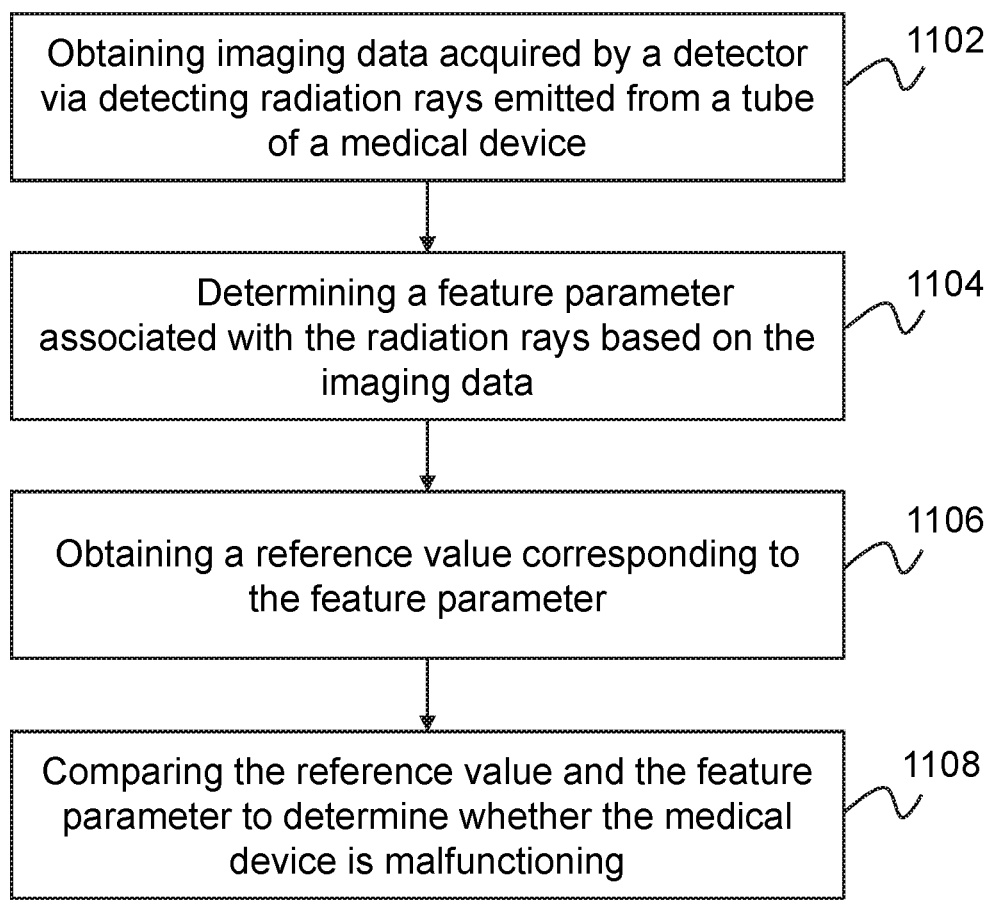
FIG. 11 is a flowchart illustrating an exemplary process for monitoring a medical device according to some embodiments of the present disclosure.

FIG. 11 is a flowchart illustrating an exemplary process 1100 for monitoring a medical device according to some embodiments of the present disclosure. In some embodiments, the process 1100 may be implemented in the imaging system 100 illustrated in FIG. 1. For example, the process 1100 may be stored in the storage 130 and/or the storage (e.g., the storage 420, the storage 490) as a form of instructions, and invoked and/or executed by the processing engine 120 (e.g., the processor 410 of the computing device 400 as illustrated in FIG. 3, the CPU 440 of the mobile device 500 as illustrated in FIG. 4).

In 1102, imaging data acquired by a detector via detecting radiation rays emitted from a tube of a medical device may be obtained. Operation 1102 may be performed by the acquisition module 831. More descriptions of the acquisition of image data may be found elsewhere in the present disclosure (e.g., operation 902 in FIG. 9 and descriptions thereof).

In 1104, a feature parameter associated with the radiation rays may be determined based on the imaging data. Operation 1104 may be performed by the calculating unit 8321 and/or the parameter determination unit 8322.

In some embodiments, the feature parameter associated with the radiation rays may include intensity parameter associated with the radiation rays, a parameter of a focus of the radiation rays, etc. The intensity parameter associated with the radiation rays may include a maximum intensity of radiation rays received by one of a plurality of detecting units in the detector, a minimum intensity of radiation rays received by one of the plurality of detecting units, an average intensity of radiation rays received by the plurality of detecting units, or the like, or any combination thereof, as described elsewhere in the present disclosure (e.g., FIG. 9 and descriptions thereof). The parameter of the focus may include a position of the focus, a size of the focus, a shape of the focus, a vibration frequency of the focus, a vibration amplitude of the focus, etc., as described elsewhere in the present disclosure (e.g., FIG. 9 and descriptions thereof).

Figure 17:
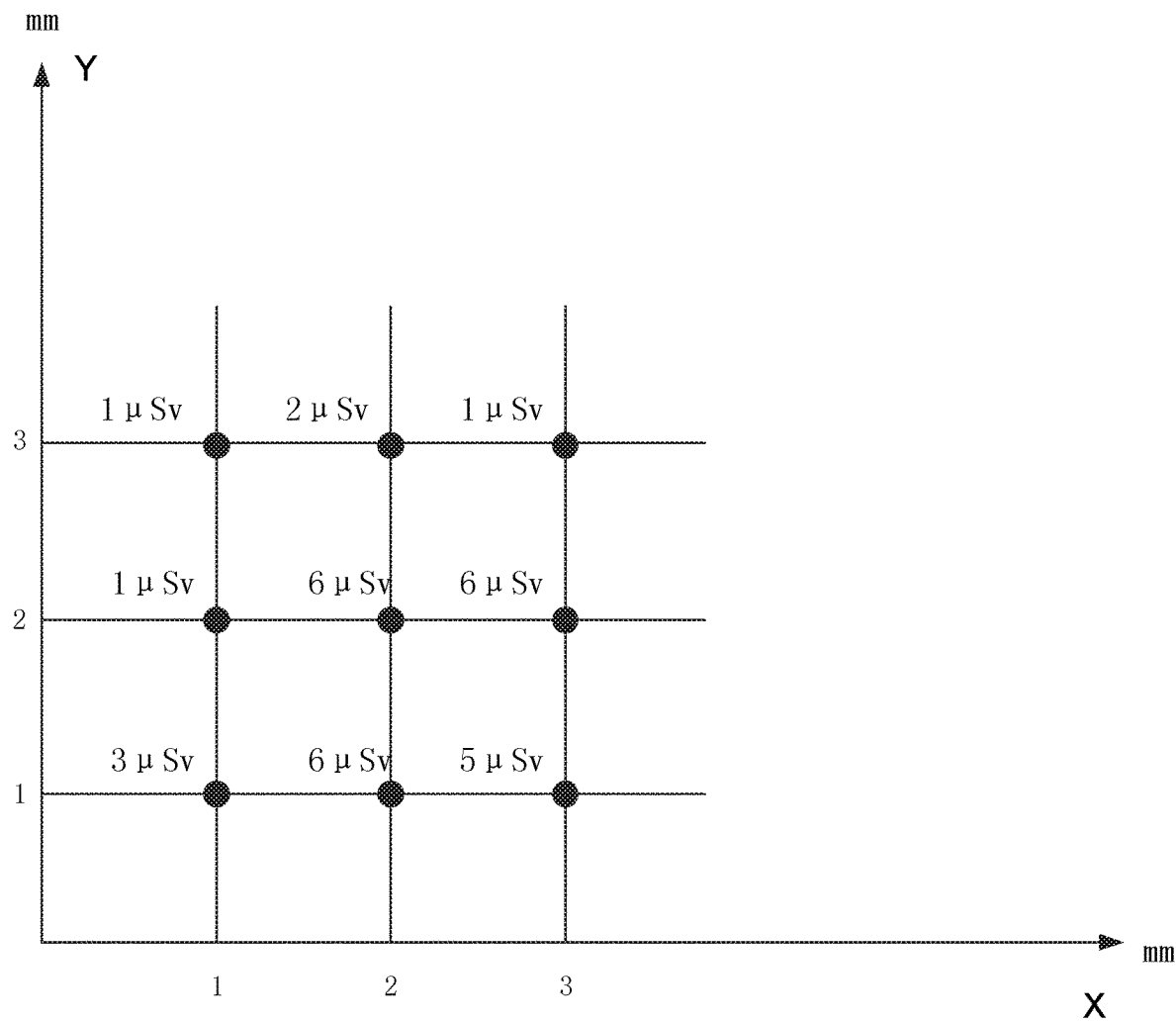
FIG. 17 is a schematic diagram illustrating an exemplary intensity distribution of the radiation rays according to some embodiments of the present disclosure.

In some embodiments, the calculating unit 8321 may determine an intensity distribution of the radiation rays received by a plurality of detecting units based on the imaging data. For example, the calculating unit 8321 may determine the intensity distribution of the radiation rays received by the plurality of detecting units based on the intensity of radiation rays received by each of the plurality of detecting units and the position of each of the plurality of detecting units. Then the parameter determination unit 8322 may determine feature parameter (e.g., the intensity parameter, the parameter of the focus, etc.) associated with the radiation rays based on the intensity distribution of the radiation rays relative to the plurality of detecting units of the detector. In some embodiments, the parameter determination unit 8322 may determine the maximum intensity or the minimum intensity of radiation rays received by one of the plurality of detecting units by comparing the intensity of radiation rays received by each of the plurality of detecting units according to, for example, a sequence (e.g., rows or columns of the detector). For example, as illustrated in FIG. 17, the parameter determination unit 8322 may determine that the maximum intensity of radiation rays received by the plurality of detecting units is 6 μSv and the minimum intensity of radiation rays received by one of the plurality of detecting units is 1 μSv.

Figure 18:
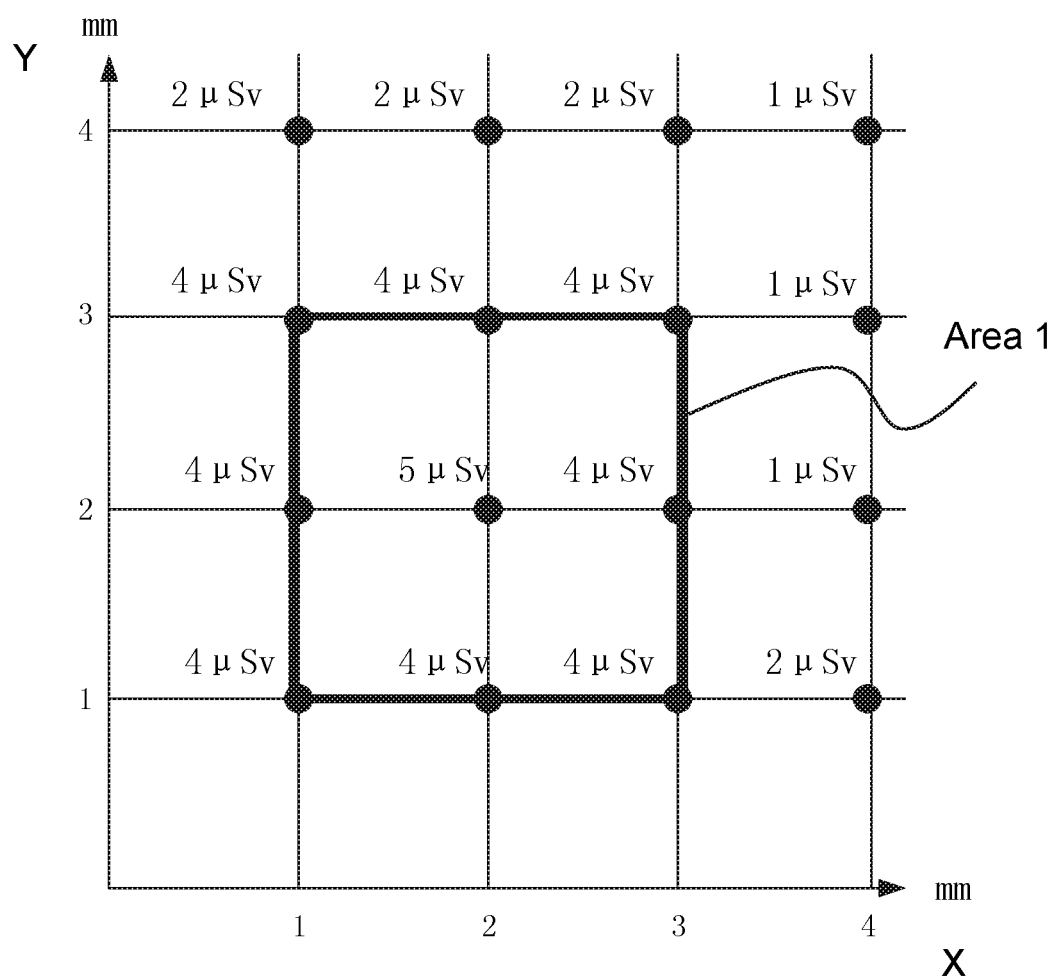
FIG. 18 is a schematic diagram illustrating an exemplary process for determining a size of a focus of the radiation rays according to some embodiments of the present disclosure.
Figure 20:
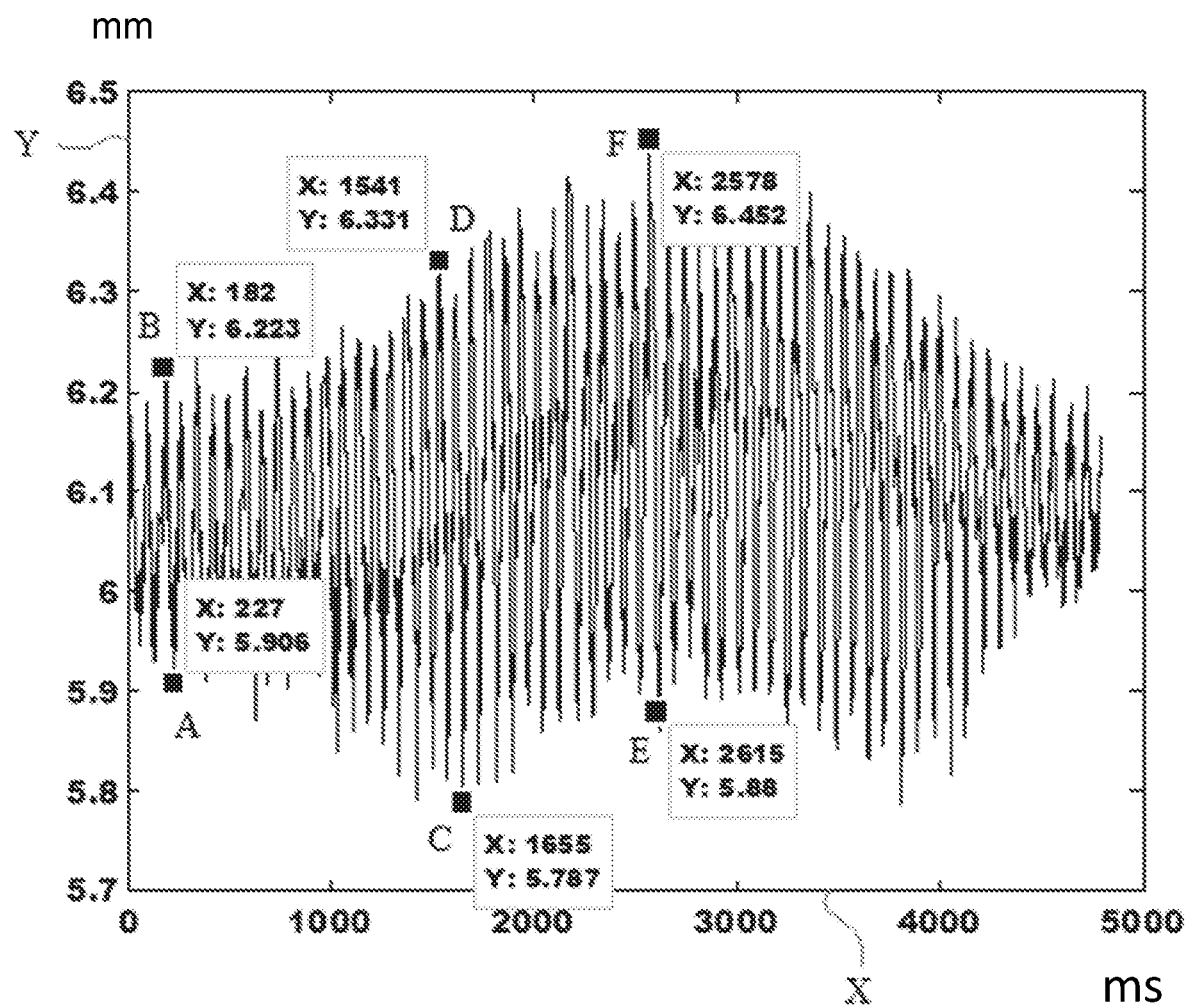
FIG. 20 is a schematic diagram illustrating an exemplary process for determining a vibration amplitude of a focus associated with the radiation rays according to some embodiments of the present disclosure.

In some embodiments, the parameter determination unit 8322 may determine the parameter of the focus based on the intensity of radiation rays received by at least one portion of the plurality of detecting units. For example, the parameter determination unit 8322 may determine the position of the focus based on the position of a detecting units with the maximum intensity. As another example, the parameter determination unit 8322 may determine the size of focus based on an area of a region of detecting units around the position of the focus. The intensity of radiation rays received by detecting units in the region may exceeds a threshold. The parameter determination unit 8322 may designate the area of the region as the size of the focus. As illustrated in FIG. 18, the parameter determination unit 8322 may determine that the size of the focus is 4 mm². As still another example, the parameter determination unit 8322 may determine a change cycle of the position of the focus determined based on the intensity distribution of the radiation rays, and determine the vibration frequency of the focus based on the change cycle of the position of the focus. The vibration frequency of the focus may be in inverse proportion to the change cycle of the position of the focus. As a further example, the parameter determination unit 8322 may determine the change of the position of the focus during the change cycle and determine the vibration amplitude of the focus based on the change of the position of the focus during the change cycle. As illustrated in FIG. 20, the vibration amplitude of the focus may be determined based on several feature points on a position change diagram, such as a distance between a highest point (e.g., point F) and a lowest point (e.g., point C) along the longitudinal axis during a change cycle.

In 1106, a reference value corresponding to the feature parameter may be obtained. Operation 1106 may be performed by the reference value acquisition unit 8323.

The reference value corresponding to the feature parameter may be determined based on a plurality of experiments. The reference value may be a desired value of the feature parameter associated with the radiation rays when the medical device is functioning well. For example, the desired value of the maximum intensity of radiation rays received by one of the plurality of detecting units may be between 4 μSv and 5 μSv when the medical device is functioning well. Accordingly, the reference value acquisition unit 8323 may determine that the reference value (e.g., a reference maximum intensity of radiation rays received by one of the plurality of detecting units) corresponding to the maximum intensity of radiation rays may be 4.5 μSv. As another example, the desired value of the size of the focus may be between 4.4 mm² and 4.8 mm² when the medical device is functioning well. The reference value acquisition unit 8323 may determine that the reference value corresponding to the size of focus may be 4.6 mm².

In 1108, the reference value and the feature parameter may be compared to determine whether the medical device is malfunctioning. Operation 1108 may be performed by the judging unit 8324. In some embodiments, since the intensity of radiation rays received by the plurality of detecting units may be determined based on the number of radiation rays emitted by the tube, high voltage, tube current loaded in the medical device, etc., the processing module 832 may determine whether the medical device is malfunctioning based on the intensity distribution of the radiation rays. For example, a tube malfunction and/or a power supply malfunction (e.g., the voltage loaded on the medical device is too high) in the medical device may increase (or decrease) the number of radiation rays per unit area, which may increase (or decrease) the intensity of radiation rays received by the plurality of detecting units. As another example, since the focus of the radiation rays may be generated by electron beam bombarding the anode target, the unstable of the focus may influence the number of radiation rays received by each detecting unit of the detector, and further influence the intensity of radiation rays received by the plurality of detecting units. The processing module 832 may determine whether the medical device (e.g., the filament of the tube, the anode target of the tube) is malfunctioning based on the size of the focus, the position of the focus, the shape of the size, or any other parameter of the focus. In some embodiments, the judging unit 8324 may determine whether the medical device is malfunctioning based on the difference between the reference value and the feature parameter and a first range or a first threshold. The judging unit 8324 may determine a difference between the reference value and the feature parameter. For example, the judging unit 8324 may determine the difference by subtracting the reference maximum intensity of radiation rays received by one of the plurality of detecting units (e.g., 4.5 μSv) from the maximum intensity of radiation rays received by one of the plurality of detecting units (e.g., 6 μSv). If the difference (e.g., 1.5 μSv) between the reference maximum intensity of radiation rays (e.g., 4.5 μSv) and the maximum intensity of radiation rays (e.g., 6 μSv) received by one of the plurality of detecting units exceeds the first threshold (e.g., 1 μSv), the judging unit 8324 may determine that the medical device is malfunctioning. As another example, for the maximum intensity of radiation rays, the first range may be [−0.5 μSv, 0.5 μSv]. The judging unit 8324 may determine whether the difference (e.g., 1.5 μSv) between the reference maximum intensity of radiation rays (e.g., 4.5 μSv) and the maximum intensity of radiation rays (e.g., 6 μSv) exceeds the first range. In response to a determination that the difference (e.g., 1.5 μSv) exceeds the first range (e.g., [−0.5 μSv, 0.5 μSv]), the judging unit 8324 may determine that the medical device is malfunctioning.

The first range and/or the first threshold may be preset manually by a user, or may be determined by one or more components of the imaging system 100 according to different situations. For example, the first range for the maximum intensity of radiation rays may be [−0.5 μSv, 0.5 μSv]. The first threshold for the maximum intensity of radiation rays may be 1 μSv.

In some embodiments, the processing module 832 may determine malfunctioning information of the medical device based on the feature parameter and the reference value directly. For example, if the first feature parameter (e.g., the vibration speed of the focus, the vibration frequency of the focus, etc.) exceeds the reference value, the judging unit 8324 may determine that the medical device is malfunctioning.

In some embodiments, the processing module 832 may further determine malfunctioning information of the medical device based on the feature parameter associated with the radiation rays. The malfunctioning information of the medical device may include the type of a malfunction, a malfunctioning component, a recommendation for eliminating the malfunction, etc., as described elsewhere in the present disclosure. For example, the malfunctioning information of the medical device may be determined based on the size of the focus. A filament malfunction and/or an anode target malfunction (e.g., the anode target is damaged) may decrease the number of the radiation rays, which may decrease the size of the focus of the radiation rays. As another example, the processing module 832 may determine malfunctioning information of the medical device based on the position of the focus and the reference position of the focus. For example, the filament malfunction (e.g., the filament is short circuit) may result in an uneven distribution of the radiation rays. As still another example, the anode target malfunction (e.g., an anode target offset) may cause the position of the focus offset.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 12:
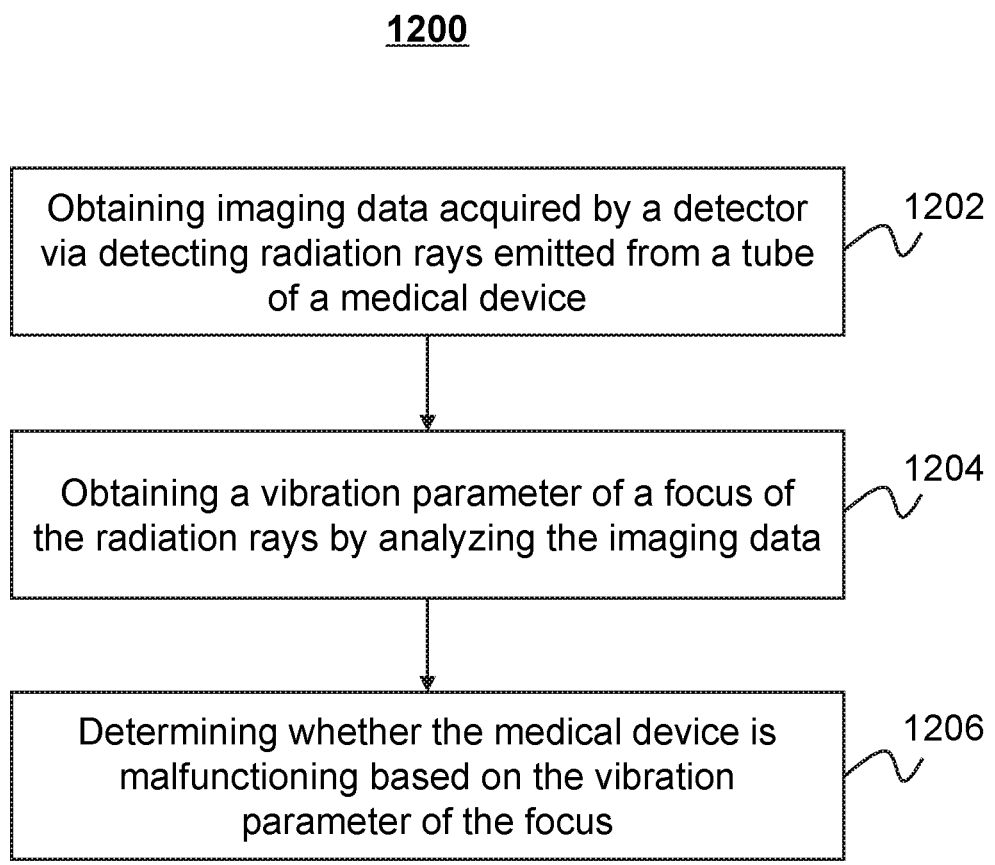
FIG. 12 is a flowchart illustrating an exemplary process for monitoring a medical device based on a vibration parameter of a focus according to some embodiments of the present disclosure.

FIG. 12 is a flowchart illustrating an exemplary process 1200 for monitoring a medical device based on a vibration parameter of a focus according to some embodiments of the present disclosure. In some embodiments, the process 1200 may be implemented in the imaging system 100 illustrated in FIG. 1. For example, the process 1200 may be stored in the storage 130 and/or the storage (e.g., the storage 420, the storage 490) as a form of instructions, and invoked and/or executed by the processing engine 120 (e.g., the processor 410 of the computing device 400 as illustrated in FIG. 3, the CPU 440 of the mobile device 500 as illustrated in FIG. 4).

In 1202, imaging data acquired by a detector via detecting radiation rays emitted from a tube of a medical device may be obtained. Operation 1202 may be performed by the acquisition module 831. More descriptions of the acquisition of image data may be found elsewhere in the present disclosure (e.g., operation 902 in FIG. 9, operation 1102 in FIG. 11, and descriptions thereof).

In 1204, a vibration parameter of a focus of the radiation rays may be obtained by analyzing the imaging data. Operation 1204 may be performed by the calculating unit 8321 and/or the parameter determination unit 8322. In some embodiments, the vibration parameter of the focus of the radiation rays may include a vibration frequency of the focus, a vibration amplitude of the focus, or the like, or any combination thereof.

In some embodiments, the parameter determination unit 8322 may determine a position of the focus of the radiation rays based on an intensity distribution of the radiation rays as described elsewhere in the present disclosure (e.g., FIGS. 9, 11 and 17, and descriptions thereof). The parameter determination unit 8322 may determine a change cycle of the position of the focus based on the position of the focus. The parameter determination unit 8322 may determine the vibration frequency of the focus based on the change cycle of the position of the focus. More descriptions of the determination of the vibration frequency of the focus may be found elsewhere in the present disclosure (e.g., FIG. 13 and descriptions thereof).

In some embodiments, the parameter determination unit 8322 may determine a change of the position of the focus in the change cycle. The parameter determination unit 8322 may determine the vibration amplitude of the focus based on the change of the position of the focus in the change cycle. More descriptions of the determination of the vibration amplitude of the focus may be found elsewhere in the present disclosure (e.g., FIG. 14 and descriptions thereof).

In 1206, a determination may be made as to determine whether the medical device is malfunctioning based on the vibration parameter of the focus. Operation 1206 may be performed by the judging unit 8324. In some embodiments, the judging unit 8324 may determine a desired value of the vibration parameter of the focus when the medical is functioning well. The desired value of the vibration parameter of the focus may also be referred to as a reference value. In some embodiments, the judging unit 8324 may determine whether the medical device is malfunctioning by comparing the vibration parameter of the focus and the reference value corresponding to the vibration parameter of the focus. For example, the judging unit 8324 may determine whether the medical device is malfunctioning by comparing the vibration frequency of the focus and the reference value corresponding to the vibration frequency of the focus. If the vibration frequency of the focus exceeds the reference value corresponding to the vibration frequency of the focus, the judging unit 8324 may determine that the medical device is malfunctioning.

In some embodiments, the judging unit 8324 may determine a difference between the vibration parameter of the focus and a reference value corresponding to the vibration parameter. The judging unit 8324 may determine whether the medical device is malfunctioning based on the difference and a threshold. For example, if a difference between the vibration amplitude of the focus and a reference value corresponding to the vibration amplitude of the focus exceeds a threshold or a range, the judging unit 8324 may determine that the medical device is malfunctioning.

In some embodiments, the processing module 832 may determine a parameter of a component in the medical device based on the vibration parameter of the focus. For example, the processing module 832 may determine a rotation speed of the anode target based on the vibration frequency of the focus. As another example, the processing module 832 may determine a vibration amplitude of the anode target based on the vibration amplitude of the focus. The judging unit 8324 may determine whether the anode target is malfunctioning based on the rotation speed of the anode target and/or the vibration amplitude of the anode target. More descriptions for determining whether the anode target is malfunctioning based on the rotation speed of the anode target and/or the vibration amplitude of the anode target may be found elsewhere in the present disclosure (e.g., FIGS. 13, 14, and descriptions thereof).

In some embodiments, the judging unit 8324 may determine whether a filament of the tube is malfunctioning based on a position of the focus, a size of the focus, the vibration frequency of the focus, the vibration amplitude of the focus, and/or an intensity distribution of the radiation rays received by a plurality of detecting units. Accordingly, the processing module 832 may monitor the medical device by analyzing operating states of one or more components of the medical device.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 13:
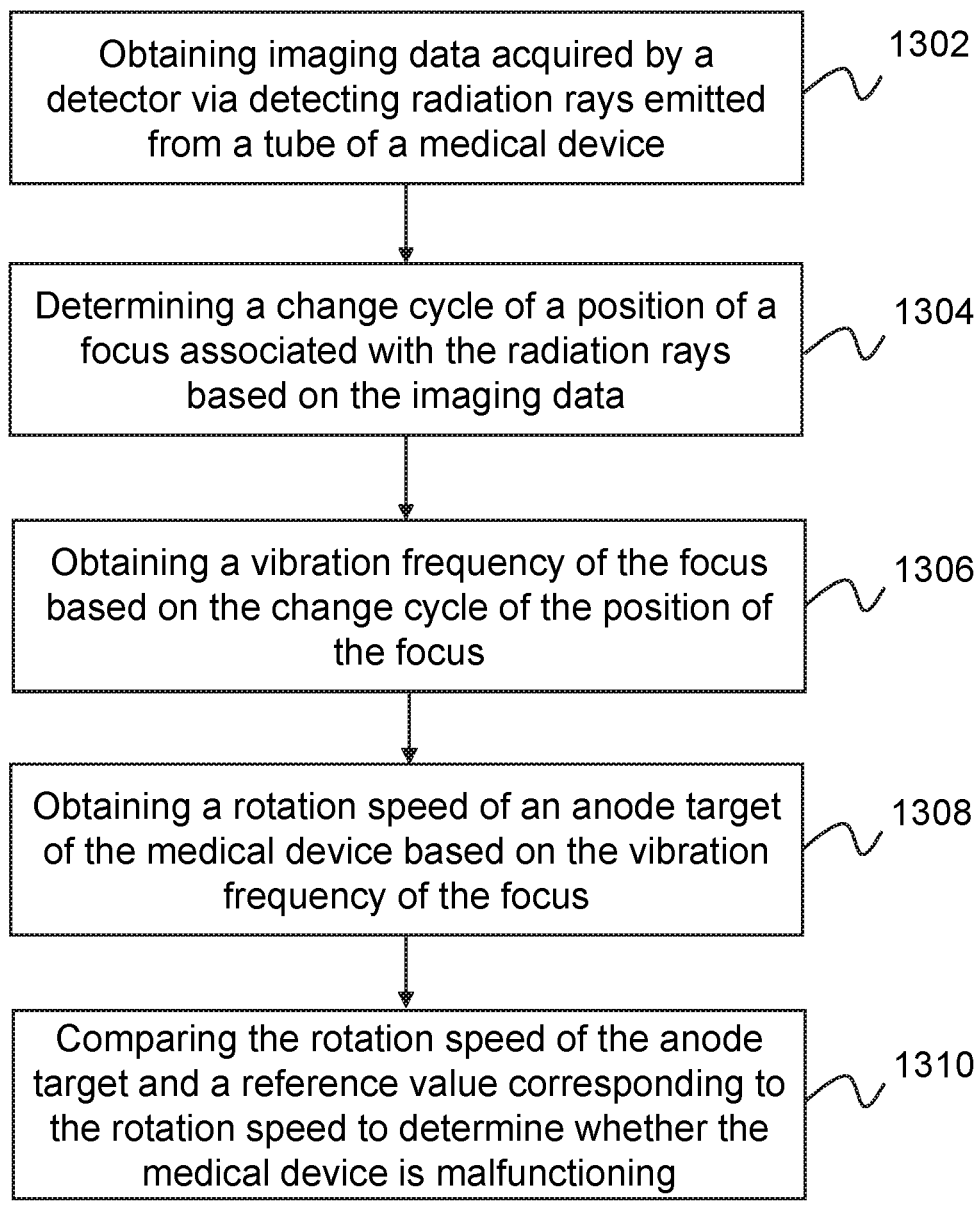
FIG. 13 is a flowchart illustrating an exemplary process for monitoring a medical device according to some embodiments of the present disclosure.

FIG. 13 is a flowchart illustrating an exemplary process 1300 for monitoring a medical device according to some embodiments of the present disclosure. In some embodiments, the process 1300 may be implemented in the imaging system 100 illustrated in FIG. 1. For example, the process 1300 may be stored in the storage 130 and/or the storage (e.g., the storage 420, the storage 490) as a form of instructions, and invoked and/or executed by the processing engine 120 (e.g., the processor 410 of the computing device 400 as illustrated in FIG. 3, the CPU 440 of the mobile device 500 as illustrated in FIG. 4).

In 1302, imaging data acquired by a detector via detecting radiation rays emitted from a tube of a medical device may be obtained. Operation 1302 may be performed by the acquisition module 831. More descriptions of the acquisition of image data may be found elsewhere in the present disclosure (e.g., operation 9002 in FIG. 9, operation 1102 in FIG. 11, operation 1202 in FIG. 12, and descriptions thereof).

In 1304, a change cycle of a position of a focus associated with the radiation rays may be determined based on the imaging data. Operation 1304 may be performed by the calculating unit 8321 and/or the parameter determination unit 8322. In some embodiments, the position of the focus may change periodically over time. As used herein, the change cycle of the position of the focus may refer to a duration of time of one cycle in the change of the position of the focus. In some embodiments, the parameter determination unit 8322 may determine the change cycle of the position of the focus based on a plurality of positions of the focus at different time points during a period of time. For example, the parameter determination unit 8322 may determine a position change diagram, as illustrated in FIG. 20, based on the plurality of positions of the focus at different time points during the period of time. The parameter determination unit 8322 may determine a duration of time corresponding a repeated curve (i.e., the duration of time of one cycle) in the position change diagram as the change cycle of the position of the focus.

In 1306, a vibration frequency of the focus may be obtained based on the change cycle of the position of the focus. Operation 1306 may be performed by the calculating unit 8321 and/or the parameter determination unit 8322. As used herein, the vibration frequency of the focus may refer to the number of cycles in a unit time period. In some embodiments, the parameter determination unit 8322 may determine the vibration frequency of the focus based on the change cycle of the position of the focus. For example, the vibration frequency of the focus may be a reciprocal of the change cycle of the position of the focus.

In 1308, a rotation speed of an anode target of the medical device may be obtained based on the vibration frequency of the focus. Operation 1308 may be performed by the calculating unit 8321 and/or the parameter determination unit 8322.

In some embodiments, the anode target may wobble around an axis, for example, the center axis of the tube in a vertical direction or horizontal direction, when the medical device is operating. The rotation speed of the anode target may be determined based on the vibration frequency of the anode target when rotating. Further, the rotation speed of the anode target may be proportional to the vibration frequency of the anode target when rotating. As the focus may be generated on the anode target by electrons emitted by the filament of the tube bombarding the anode target. The vibration frequency of the anode target may be same as or similar to the vibration frequency of the focus, for example, proportional to the vibration frequency of the focus. Thus, the vibration frequency of the anode target may be determined based on the vibration frequency of the focus.

In 1310, the rotation speed of the anode target and a reference value corresponding to the rotation speed may be compared to determine whether the medical device is malfunctioning. Operation 1310 may be performed by the judging unit 8324. The reference value corresponding to the rotation speed may be a desired value of the rotation speed of the anode target when the medical device is functioning well. The reference value corresponding to the rotation speed (i.e., a reference rotation speed) may be preset manually by a user, or may be determined by one or more components of the imaging system 100 according to different situations. In some embodiments, the reference value corresponding to the rotation speed may be a rated speed of the anode target determined based on mechanical properties of the medical device.

In some embodiments, the judging unit 8324 may determine a difference between the rotation speed of the anode target and the reference value. The judging unit 8324 may determine whether the medical device is malfunctioning based on the difference between the rotation speed of the anode target and the reference value and a threshold. For example, the judging unit 8324 may determine whether the difference between the rotation speed of the anode target and the reference value exceeds the threshold. In response to a determination that the difference between the rotation speed of the anode target and the reference value exceeds the threshold, the judging unit 8324 may determine that the medical device is malfunctioning.

In some embodiments, the judging unit 8324 may determine a service life of the tube based on the difference between the rotation speed of the anode target and the speed threshold. For example, the judging unit 8324 may predetermine a relationship between the service life of the tube and the difference between the rotation speed of the anode target with the reference value (i.e., the desired value). The judging unit 8324 may determine the service life of the tube based on the relationship.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 14:
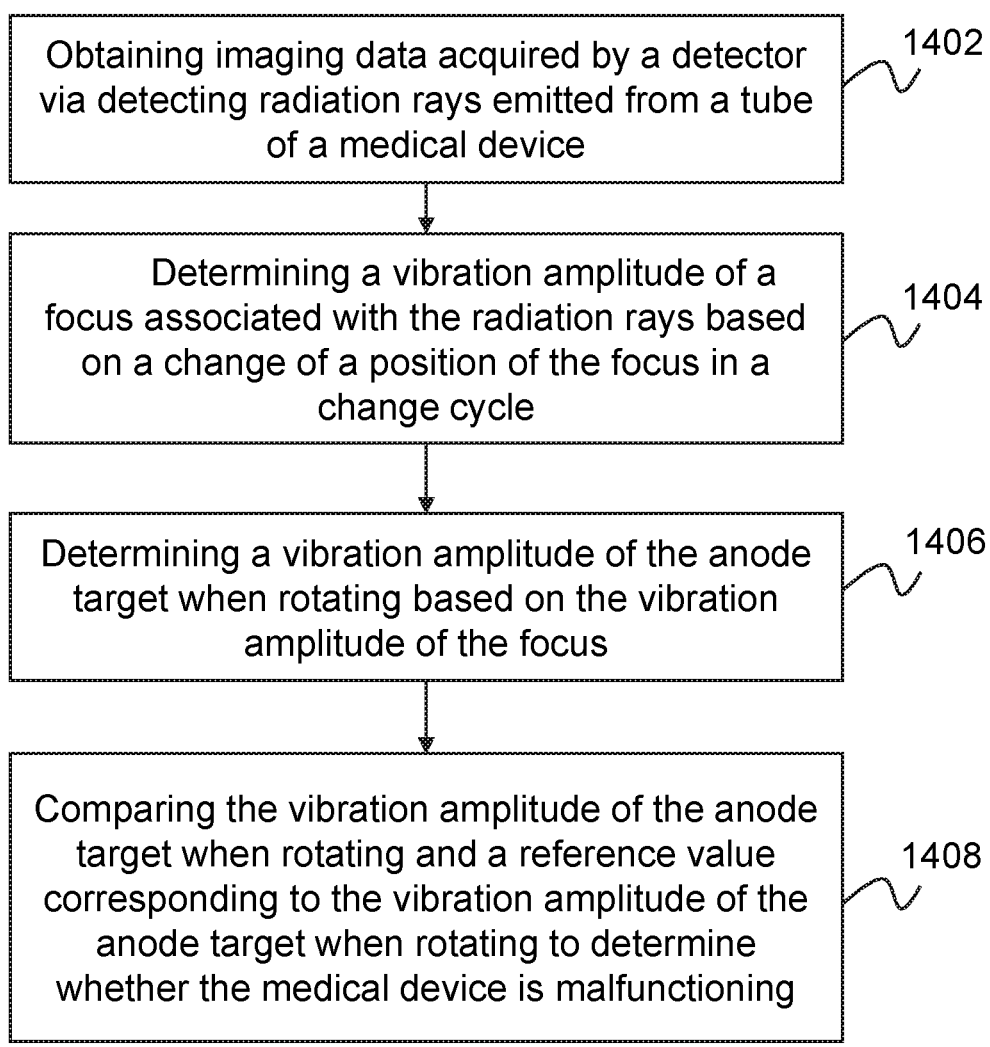
FIG. 14 is a flowchart illustrating an exemplary process for monitoring a medical device according to some embodiments of the present disclosure.

FIG. 14 is a flowchart illustrating an exemplary process 1400 for monitoring a medical device according to some embodiments of the present disclosure. In some embodiments, the process 1400 may be implemented in the imaging system 100 illustrated in FIG. 1. For example, the process

1400 may be stored in the storage 130 and/or the storage (e.g., the storage 420, the storage 490) as a form of instructions, and invoked and/or executed by the processing engine 120 (e.g., the processor 410 of the computing device 400 as illustrated in FIG. 3, the CPU 440 of the mobile device 500 as illustrated in FIG. 4).

In 1402, imaging data acquired by a detector via detecting radiation rays emitted from a tube of a medical device may be obtained. Operation 1402 may be performed by the acquisition module 831. More descriptions of the acquisition of image data may be found elsewhere in the present disclosure (e.g., operation 902 in FIG. 9, operation 1102 in FIG. 11, operation 1202 in FIG. 12, operation 1302 in FIG. 13, and descriptions thereof).

In 1404, a vibration amplitude of a focus associated with the radiation rays may be determined based on a change of a position of the focus in a change cycle. Operation 1404 may be performed by the calculating unit 8321 and/or the parameter determination unit 8322. More descriptions for determining the vibration amplitude of the focus may be found elsewhere in the present disclosure (e.g., FIGS. 9, 10, and 20, and descriptions thereof).

In 1406, a vibration amplitude of an anode target when rotating may be determined based on the vibration amplitude of the focus. Operation 1406 may be performed by the calculating unit 8321 and/or the parameter determination unit 8322.

As used herein, a vibration amplitude of an anode target when rotating may refer to a wobbling angle when the anode target operating. In some embodiments, the vibration amplitude of the anode target when rotating may equal to the vibration amplitude of the rotation of the focus.

In 1408, the vibration amplitude of the anode target when rotating and a reference value corresponding to the vibration amplitude of the anode target when rotating may be compared to determine whether the medical device is malfunctioning. Operation 1408 may be performed by the judging unit 8324.

The reference value corresponding to the vibration amplitude of the anode target when rotating may be a desired value of the vibration amplitude of the anode target when rotating when the medical device is functioning well. The reference value corresponding to the vibration amplitude of the anode target when rotating (i.e., a reference vibration amplitude) may be preset manually by a user, or may be determined by one or more components of the imaging system 100 according to different situations. In some embodiments, the reference value corresponding to the vibration amplitude of the anode target when rotating may be a rated vibration amplitude of the anode target when rotating determined based on mechanical properties of the medical device.

In some embodiments, the judging unit 8324 may determine a difference between the vibration amplitude of the anode target when rotating and the reference value. The judging unit 8324 may determine whether the medical device is malfunctioning based on the difference between the vibration amplitude of the anode target when rotating and the reference value and a threshold. For example, the judging unit 8324 may determine whether the difference between the vibration amplitude of the anode target when rotating and the reference value exceeds the threshold. In response to a determination that the difference between the vibration amplitude of the anode target when rotating and the reference value exceeds the threshold, the judging unit 8324 may determine that the medical device is malfunctioning.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 15:
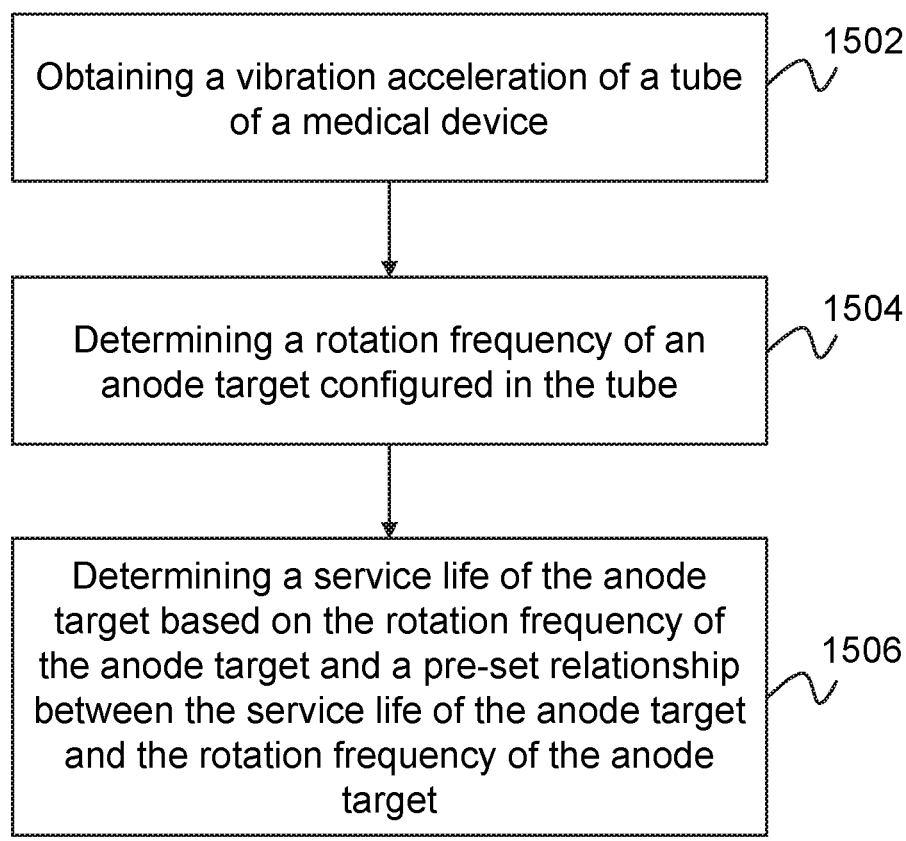
FIG. 15 is a flowchart illustrating an exemplary process for determining a service life of an anode target according to some embodiments of the present disclosure.

FIG. 15 is a flowchart illustrating an exemplary process 1500 for determining a service life of an anode target according to some embodiments of the present disclosure. In some embodiments, the process 1500 may be implemented in the imaging system 100 illustrated in FIG. 1. For example, the process 1500 may be stored in the storage 130 and/or the storage (e.g., the storage 420, the storage 490) as a form of instructions, and invoked and/or executed by the processing engine 120 (e.g., the processor 410 of the computing device 400 as illustrated in FIG. 3, the CPU 440 of the mobile device 500 as illustrated in FIG. 4).

In 1502, a vibration acceleration of a tube of a medical device may be obtained. Operation 1502 may be performed by the sensor 602. In some embodiments, the sensor 602 may obtain the vibration acceleration of the tube continuously or periodically (e.g., every 3 seconds).

In some embodiments, the sensor 602 may be a vibration sensor (e.g., an acceleration sensor) configured on a shell of the tube. In some embodiments, the rotating of an anode target configured in the tube may be driven by a motor, which may cause a vibration of the shell of the tube. The sensor 620 may obtain an acceleration signal of the shell of the tube when the anode target rotates. The vibration acceleration of the tube may be determined based on the acceleration signal.

In 1504, a rotation frequency of the anode target configured in the tube may be determined. Operation 1504 may be performed by the processor 604.

As used herein, a rotation frequency of the anode target may refer to the number of turns of the anode target in a unit time. In some embodiments, the processor 604 may perform one or more operations on the vibration acceleration of the tube to determine the rotation frequency of the anode target. For example, the processor 604 may perform a transform operation on the vibration acceleration of the tube to determine spectrum information associated with the rotation frequency of the anode target. Merely by ways of example, the transform operation may include a Fourier transform. The processor 604 may determine the rotation frequency of the anode target based on the spectrum information associated with the rotation frequency of the anode target.

In 1506, a service life of the anode target may be determined based on the rotation frequency of the anode target and a pre-set relationship between the service life of the anode target and the rotation frequency of the anode target. Operation 1506 may be performed by the monitor 606.

As used herein, a service life may refer to a period of use in service. The service life may be a total life in use from the time of sale to the time of discard, or a remaining life in use. In some embodiments, the pre-set relationship between the service life of the anode target and the rotation frequency of the anode target may be determined based on historical data associated with the service life of the anode target and the rotation frequency of the anode target. For example, the historical data associated with the service life of the anode target and the rotation frequency of the anode target may include the rotation frequencies of one or more reference anode targets and corresponding service lives, operating states, such as the rotation frequency of a reference anode target when the reference anode target retires and the correspond service life. The pre-set relationship between the service life of the anode target and the rotation frequency of the anode target may be determined by performing a polynomial fitting or linear fitting based on the historical data associated with the service life of the anode target and the rotation frequency of the anode target.

In some embodiments, the pre-set relationship between the service life of the anode target and the rotation frequency of the anode target may be stored in a storage device (e.g., the storage 130) of the imaging system 100 or an external storage device. The monitor 606 may access the storage device and retrieve the pre-set relationship between the service life of the anode target and the rotation frequency of the anode target.

In some embodiments, the service life of the anode target may be transmitted to a client terminal (e.g., the client terminal 140) for display. The service life of the anode target may be presented in the client terminal in the form of text, audio, graph, video, or the like, or any combination thereof. For example, a text message, a voice message, or a video message including the service life of the anode target may be transmitted to the client terminal 140.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, one or more other optional operations (e.g., a storing step) may be added elsewhere in the exemplary process 1500. For a further example, process 1500 may further include storing information and/or data associated with the tube. The processing engine 112 may store the information and/or data associated with the tube in a storage medium (e.g., the storage 130), which is disclosed elsewhere in the present disclosure.

Figure 16:
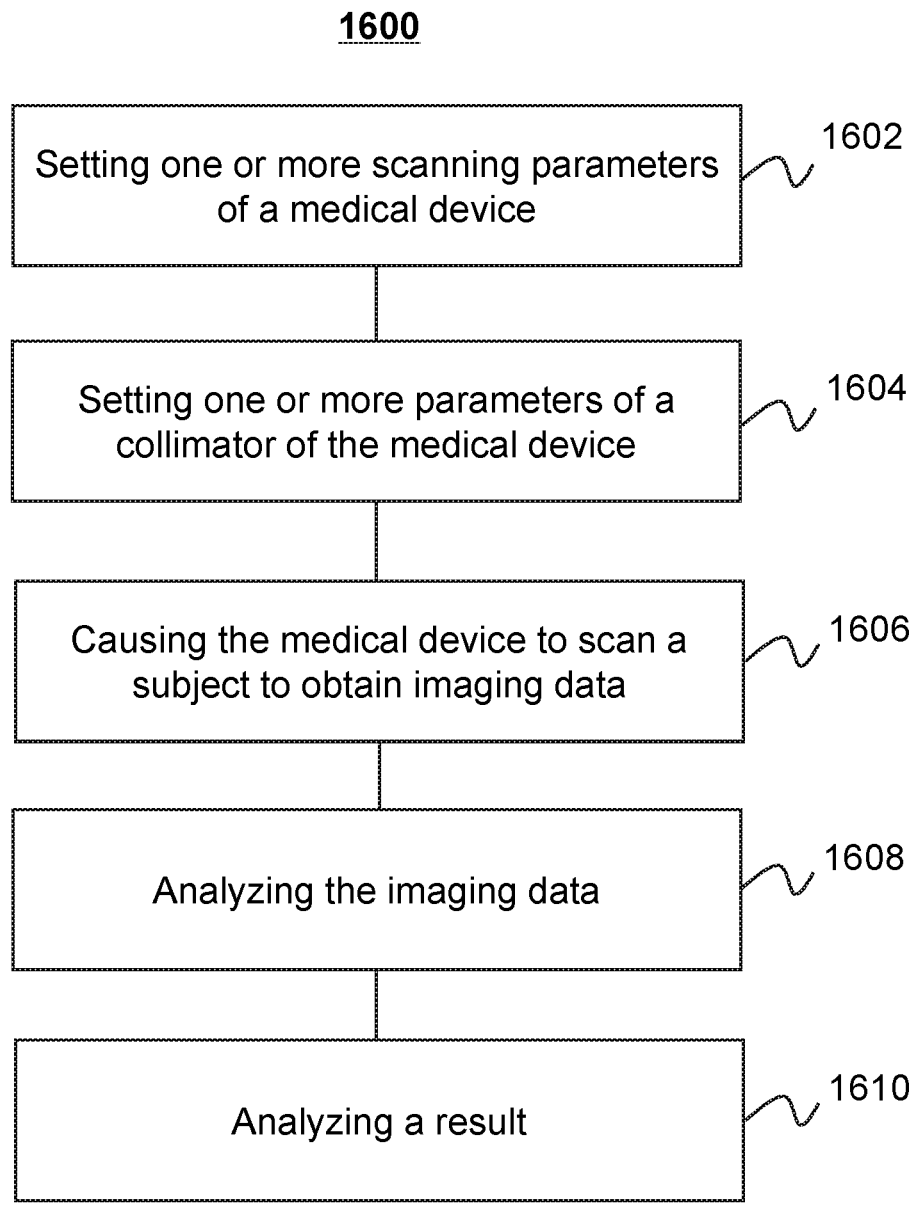
FIG. 16 is a flowchart illustrating an exemplary process for monitoring a medical device according to some embodiments of the present disclosure.

FIG. 16 is a flowchart illustrating an exemplary process 1600 for monitoring a medical device according to some embodiments of the present disclosure. In some embodiments, the process 1600 may be implemented in the imaging system 100 illustrated in FIG. 1. For example, the process 1600 may be stored in the storage 130 and/or the storage (e.g., the storage 420, the storage 490) as a form of instructions, and invoked and/or executed by the processing engine 120 (e.g., the processor 410 of the computing device 400 as illustrated in FIG. 3, the CPU 440 of the mobile device 500 as illustrated in FIG. 4).

In 1602, one or more scanning parameters of a medical device may be set. The one or more scanning parameters of the medical device may be determined by one or more components of the imaging system 100 (e.g., the processing module 832) or be set by an operator (e.g., a doctor, a technician) via the client terminal 140 according to different situations.

In some embodiments, the one or more scanning parameters of the medical device may be set before performing a scan. The scanning parameters may include a scan current, a scan voltage, a scan time, or the like, or any combination thereof. Merely by way of example, the scan voltage may be 1.2 KV and the scan current may be 80 mA. The scan time may be 4.5 seconds, that is, the tube may emit radiation rays for 4.5 seconds and then stop working.

In 1604, one or more parameters of a collimator of the medical device may be set. The one or more parameters of the collimator may be determined by one or more components of the imaging system 100 (e.g., the processing module 832) or be set by an operator via the client terminal 140 according to different situations.

In some embodiments, the parameter of the collimator may include a position of an opening of the collimator, a collimating width of the collimator, or the like, or any combination thereof. The collimator may be configured to limit or collimate the radiation rays emitted from the tube. In some embodiments, the processing module 832 may adjust the one or more parameters of the collimator (e.g., the collimator 250) such that the radiation rays emitted by the tube (e.g., the tube 260) can all be received by a detector (e.g., the detector 240) after being collimated by the collimator.

In 1606, the medical device may be caused to scan a subject to obtain imaging data. Operation 1606 may be performed by the processing module 832 and/or the console 220.

The subject may relate to an organic or inorganic mass that has a chemical, biochemical, biological, physiological, biophysical and/or physical activity or function. In some embodiments, the subject may include cells, tissues, organs or whole body of a human or animal. In some embodiments, the subject may include a phantom.

In some embodiments, a console (e.g., the console 220) may instruct a high-voltage generator (e.g., the high-voltage generator 230) to output a high voltage. The high voltage may trigger a filament (e.g., the filament 261) to emit a large number of electrons to form an electron beam. The emitted electron beam may be impinged on a small area (i.e., the focus) on an anode target (e.g., the anode target 262) to generate X-rays beams consisting of high-energetic photons. The X-rays beams may be collimated by the collimator and project onto a surface of the detector. The detector may obtain data associated with the projection formed by the X-rays as image data (also referred to as projection data). The image data may be transmitted to the console for further processing.

In 1608, the imaging data may be analyzed. Operation 1608 may be performed by the processing module 832 and/or the console 220.

In some embodiments, the console 220 may determine an intensity distribution of the radiation rays received by a plurality of detecting units based on the image data. For example, the console 220 may determine the intensity distribution of the radiation rays received by the plurality of detecting units based on an intensity of radiation rays received by each of the plurality of detecting units and a position of each of the plurality of detecting units. In some embodiments, the console 220 may determine a feature parameter (e.g., a maximum, minimum, or average intensity of radiation rays received by the plurality of detecting units, a size of the focus, a position of the focus) associated with the radiation rays based on the intensity distribution of the radiation rays received by the plurality of detecting units as described elsewhere in the present elsewhere (e.g., FIGS. 9, 11-12, and descriptions thereof). The console 220 may obtain a reference value (e.g., a reference maximum, minimum, or average intensity of radiation rays received by the plurality of detecting units, a reference size of the focus, a reference position of the focus, etc.) corresponding to the feature parameter. The console 220 may compare the feature parameter and the reference value. The console 220 may determine whether the medical device is malfunctioning based on the comparison. For example, the console 220 may determine a difference between the feature parameter and the reference value. The console 220 may determine whether the difference between the feature parameter and the reference value exceeds a threshold. In response to a determination that the difference exceeds the threshold, the console 220 may determine that the medical device is malfunctioning.

In 1610, a result may be analyzed. Operation 1610 may be performed by the processing module 832 and/or the operator of the imaging system 100.

In some embodiments, the processing module 832 may determine malfunctioning information of the medical device based on the feature parameter and the corresponding reference value. The malfunctioning information may include the type of a malfunction, a malfunctioning component, a recommendation for eliminating the malfunction, or the like, or any combination thereof. For example, if the processing module 832 determines that the maximum intensity of radiation rays received by one of the plurality of detecting units is normal, and the position of the focus is abnormal, it may indicate that there is a power malfunction (e.g., a malfunction in the power 210) in the medical device. As another example, if the processing module 832 determines that the maximum intensity of radiation rays received by one of the plurality of detecting units is abnormal, and the position of the focus is normal, it may indicate there is a high-voltage generator malfunction (e.g., a malfunction in the high-voltage generator 230) in the medical device. As still another example, if the processing module 832 determines that the maximum intensity of radiation rays received by one of the plurality of detecting units, the position of the focus, and the size of the focus are abnormal, it may indicate that there are the high-voltage generator malfunction (e.g., a malfunction in the high-voltage generator 230) and/or a tube malfunction (e.g., a malfunction in the tube 260) in the medical device. In some embodiments, the processing module 832 may determine the malfunctioning components of the medical device based on logs and/or feedback parameters.

FIG. 17 is a schematic diagram illustrating an exemplary intensity distribution of the radiation rays according to some embodiments of the present disclosure. The detector may include a plurality of detecting units arranged in any suitable manner. As illustrated in FIG. 17, the transverse axis denotes the row of the detector, and the long longitudinal axis denotes the column of the detector. The plurality of detecting units are presented in the form of a detecting unit array, where each black dot represents a detecting unit. The detecting unit array may include a plurality of rows and columns. The coordinates of a black dot may represent the position of a detecting unit in the detector. The interval between two adjacent rows in the detecting unit array may be any suitable values, e.g., 0.5 mm, 1.0 mm, 2.0 mm, etc. The interval between two adjacent columns in the detecting unit array may be any suitable values, e.g., 0.5 mm, 1.0 mm, 2.0 mm, etc. In some embodiments, the interval between two adjacent columns may be equal to the interval between two adjacent rows. In some embodiments, at a same time point, the intensity of radiation rays received by each of the plurality of detecting units may be different. After a scan completes, the intensity of radiation rays received by each of the plurality of detecting units may be different or same. As shown in FIG. 17, the maximum intensity of radiation rays (also referred to as actual maximum intensity) may be 6 μSv received by the detecting units having coordinates (2, 1), (2, 3), and (3, 3). A desired value of a maximum intensity (i.e., reference maximum intensity) may be in a range between 4 μSv and 5 μSv when a medical device is functioning well. Further, the reference maximum intensity may be determined as 4.5 μSv. If the medical device is malfunctioning, the difference between the reference maximum intensity and the actual maximum intensity may be in a range of [−0.5 μSv, 0.5 μSv]. The difference between the reference maximum intensity 4.5 μSv and the actual maximum intensity 6 μSv exceeds the range of [−0.5 μSv, 0.5 μSv], which indicates that the medical device is malfunctioning. Further, the malfunction of the medical device may be the voltage loaded by a high-voltage generator is too high or the tube is malfunctioning.

FIG. 18 is a schematic diagram illustrating an exemplary process for determining a size of a focus of the radiation rays according to some embodiments of the present disclosure. FIG. 18 shows an intensity distribution of radiation rays received by a detector as described in FIG. 17. The position of a focus of the radiation rays may be denoted by the position of a detecting unit having coordinates (2, 2). Area 1 around the position of the focus is determined, in which the intensity of radiation rays received by each of the detecting units exceeds an intensity threshold 3 μSv. The size of Area 1 may be designated as the size of the focus. That is, the size of the focus is 4 mm² (2.0 mm×2.0 mm=4.0 mm²), also referred to as actual focus size. In some embodiments, the desired size of the focus may be between 4.4 mm² and 4.8 mm² when the medical device is functioning well. Accordingly, a reference size of the focus may be determined as 4.6 mm². The difference between the reference size of the focus and the actual focus size is −0.6 mm² (4.0 mm²−4.6 mm²=−0.6 mm²). If the medical device is malfunctioning, the difference between the reference size and the actual size may be in a range of [−0.2 mm², 0.2 mm²]. The difference −0.6 mm² exceeds the range [−0.2 mm², 0.2 mm²], which indicates that the medical device is malfunctioning.

Figure 19:
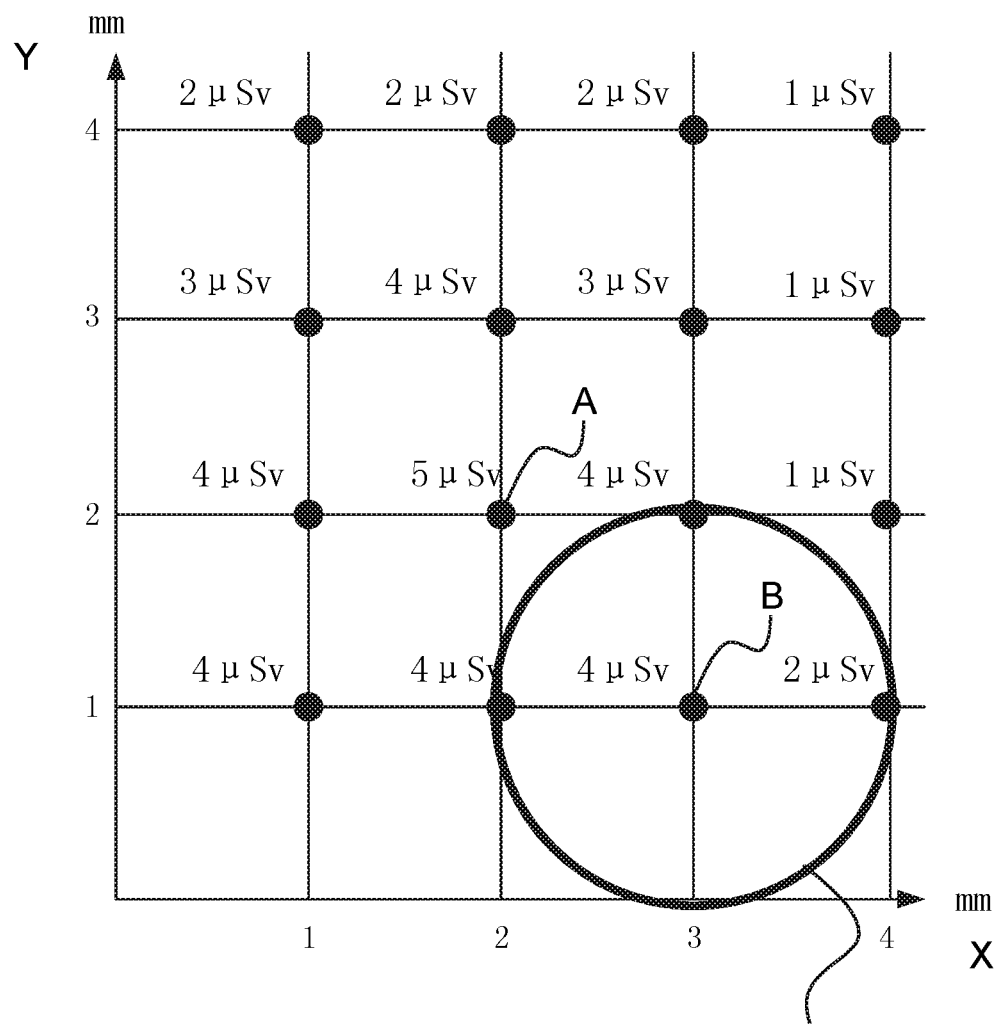
FIG. 19 is a schematic diagram illustrating an exemplary process for determining a position of a focus of the radiation rays according to some embodiments of the present disclosure.

FIG. 19 is a schematic diagram illustrating an exemplary process for determining a position of a focus of the radiation rays according to some embodiments of the present disclosure. FIG. 19 shows an intensity distribution of radiation rays received by a detector as described in FIG. 17. As illustrated in FIG. 19, a point A (2, 2) is determined as the position of the focus which has a maximum intensity, and a point B (3, 1) is determined as a reference position of the focus (or a desired focus position) when the medical device is functioning well. The distance between the point A (2, 2) and the point B (3, 1) may be $\sqrt{2}$ mm $$(\sqrt{(2-3)^2 + (2-1)^2} = \sqrt{2} \text{ mm}).$$

If the medical device is malfunctioning, an offset of the actual position of the focus from the desired focus position may be in a range of [0, 1] denoted by Area 2. The center of the Area 2 is point B, and the radius of Area 2 is 1 mm. The distance between the actual position of the focus and the reference position of the focus exceeds the range [0, 1], that is, the position of the focus is outside the Area 2. The distance $\sqrt{2}$ mm exceeds the range [0, 1], that is, the position of the focus is outside Area 2, which indicates that the medical device is malfunctioning. Further, the focus may be generated by electrons emitted by a filament bombarding an anode target. The malfunction of the medical device may be short circuit of the filament or position offset of the anode target.

FIG. 20 is a schematic diagram illustrating an exemplary process for determining a vibration amplitude of a focus associated with the radiation rays according to some embodiments of the present disclosure. As illustrated in FIG. 20, X axis refers to a change cycle of a position of a focus, and Y axis refers to a change of the position of the focus. A plurality of points, for example, a point A (227, 5.906), a point B (182, 6.223), a point C (1655, 5.787), a point D (1541, 6.331), a point E (2615, 5.88), a point F (2578, 6.452) may be determined. The vibration amplitude of the focus may be determined based on coordinates of the plurality of points. For example, a maximum amount of change of Y axis coordinates of the plurality of points in the change cycle may be determined as the vibration amplitude of the focus. As illustrated in FIG. 20, the vibration amplitude of the focus may be 0.665 mm (6.452 mm−5.787 mm=0.665 mm).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

We claim:

1. A system for monitoring a medical device including a tube configured to generate radiation rays, comprising:
a computer-readable storage medium storing executable instructions, and at least one processor in communication with the computer-readable storage medium, when executing the executable instructions, causing the system to:
obtain a vibration acceleration of the tube;

determine, based on the vibration acceleration of the tube, a rotation frequency of an anode target configured in the tube; and determine, based on the rotation frequency of the anode target, whether the anode target is malfunctioning.

2. The system of claim 1, wherein the vibration acceleration of the tube is provided by a vibration sensor mounted on a shell of the tube.

3. The system of claim 1, wherein to determine, based on the vibration acceleration of the tube, a rotation frequency of an anode target configured in the tube, the at least one processor is further configured to cause the system to:

determine spectrum information associated with the rotation frequency of the anode target by performing a transform operation on the vibration acceleration of the tube; and determine the rotation frequency of the anode target based on the spectrum information.

4. The system of claim 1, the at least one processor is further configured to cause the system to:

determine a service life of the anode target based on the rotation frequency of the anode target.

5. The system of claim 4, wherein to determine a service life of the anode target based on the rotation frequency of the anode target, the at least one processor is further configured to cause the system to:

obtain a relationship between the service life of the anode target and the rotation frequency of the anode target; and determine, based on the rotation frequency of the anode target and the relationship, the service life of the anode target.

6. The system of claim 5, wherein the relationship between the service life of the anode target and the rotation frequency of the anode target is determined based on historical data associated with various service life of the anode target and rotation frequencies of the anode target.

7. The system of claim 4, wherein to determine a service life of the anode target based on the rotation frequency of the anode target, the at least one processor is further configured to cause the system to:

obtain a relationship between the service life of the anode target and a difference between the rotation frequency of the anode target and a threshold; and determine, based on the rotation frequency of the anode target and the relationship, the service life of the anode target.

8. The system of claim 4, wherein to determine a service life of the anode target based on the rotation frequency of the anode target, the at least one processor is further configured to cause the system to:

estimate the service life of the anode target based on a parameter of a focus of the radiation rays and the rotation frequency of the anode target.

9. The system of claim 1, wherein to determine whether the anode target is malfunctioning based on the rotation frequency of the anode target, the at least one processor is further configured to cause the system to:

obtain a reference value corresponding to the rotation frequency of the anode target;

compare the reference value and the rotation frequency of the anode target; and determine whether the anode target is malfunctioning based on the comparison.

10. The system of claim 9, wherein to determine whether the anode target is malfunctioning based on the comparison, the at least one processor is further configured to cause the system to:

determine that the anode target is malfunctioning in response to a determination that a difference between the reference value and the rotation frequency exceeds a threshold.

11. The system of claim 1, wherein the at least one processor is further configured to cause the system to:

generate a malfunctioning alert in response to a determination that the anode target is malfunctioning.

12. A method for monitoring a medical device including a tube configured to generate radiation rays, the method being implemented on a system having one or more processors and a computer-readable storage medium, the method comprising:

obtain a vibration acceleration of the tube;

determine, based on the vibration acceleration of the tube, a rotation frequency of an anode target configured in the tube; and determine, based on the rotation frequency of the anode target, whether the anode target is malfunctioning.

13. The method of claim 12, wherein the determining, based on the vibration acceleration of the tube, a rotation frequency of an anode target configured in the tube includes:

determine spectrum information associated with the rotation frequency of the anode target by performing a transform operation on the vibration acceleration of the tube; and determine the rotation frequency of the anode target based on the spectrum information.

14. The method of claim 12, further comprising:

determine a service life of the anode target based on the rotation frequency of the anode target.

15. The method of claim 14, wherein the determining a service life of the anode target based on the rotation frequency of the anode target includes:

obtain a relationship between the service life of the anode target and the rotation frequency of the anode target; and determine, based on the rotation frequency of the anode target and the relationship, the service life of the anode target.

16. The method of claim 14, wherein the determining a service life of the anode target based on the rotation frequency of the anode target includes:

obtain a relationship between the service life of the anode target and a difference between the rotation frequency of the anode target and a threshold; and determine, based on the rotation frequency of the anode target and the relationship, the service life of the anode target.

17. The method of claim 14, wherein the determining a service life of the anode target based on the rotation frequency of the anode target includes:

estimate the service life of the anode target based on a parameter of a focus of the radiation rays and the rotation frequency of the anode target.

18. The method of claim 12, wherein the determining whether the anode target is malfunctioning based on the rotation frequency of the anode target includes:

obtain a reference value corresponding to the rotation frequency of the anode target;

compare the reference value and the rotation frequency of the anode target; and determine whether the anode target is malfunctioning based on the comparison.

19. The method of claim 12, further comprising:
generate a malfunctioning alert in response to a determination that the anode target is malfunctioning.

20. A non-transitory computer readable medium storing instructions, the instructions, when executed by a computer, causing the computer to implement a method, comprising:
obtain a vibration acceleration of the tube;
determine, based on the vibration acceleration of the tube, a rotation frequency of an anode target configured in the tube; and
determine, based on the rotation frequency of the anode target, whether the anode target is malfunctioning.

* * * * *